United States Patent
Ramasamy et al.

(10) Patent No.: US 11,325,873 B1
(45) Date of Patent: May 10, 2022

(54) METHOD AND SYSTEM EMBODIMENTS FOR CONVERTING ETHANOL TO PARA-XYLENE AND ORTHO-XYLENE

(71) Applicants: Battelle Memorial Institute, Richland, WA (US); LanzaTech, Inc., Skokie, IL (US)

(72) Inventors: Karthikeyan K. Ramasamy, West Richland, WA (US); Mond Guo, Richland, WA (US); Richard Russell Rosin, Glencoe, IL (US); Joseph Anthony Kocal, Glenview, IL (US)

(73) Assignees: Battelle Memorial Institute, Richland, WA (US); LanzaTech, Inc., Skokie, IL (US)

( * ) Notice: Subject to any disclaimer, the term of this patent is extended or adjusted under 35 U.S.C. 154(b) by 0 days.

(21) Appl. No.: 17/387,725

(22) Filed: Jul. 28, 2021

(51) Int. Cl.
  *C07C 1/207* (2006.01)
  *C07C 7/04* (2006.01)
  *C07C 45/68* (2006.01)

(52) U.S. Cl.
  CPC .............. *C07C 1/2076* (2013.01); *C07C 7/04* (2013.01); *C07C 45/68* (2013.01); *C07C 2521/04* (2013.01); *C07C 2521/06* (2013.01); *C07C 2521/18* (2013.01); *C07C 2523/44* (2013.01); *C07C 2523/656* (2013.01)

(58) Field of Classification Search
  CPC ......... C07C 1/2076; C07C 7/04; C07C 45/68; C07C 2521/04; C07C 2521/06; C07C 2521/18; C07C 2523/44; C07C 2523/656
  See application file for complete search history.

(56) References Cited

U.S. PATENT DOCUMENTS 3,636,157 A * 1/1972 Bozik .................. C07C 47/542
                                                   568/433
3,662,013 A    5/1972 Machell et al.
          (Continued)

FOREIGN PATENT DOCUMENTS

WO    WO 2019/117759    6/2019

OTHER PUBLICATIONS

Gonçalves et al., "Thermodynamic equilibrium of xylene isomerization in the liquid phase," *J. Chem. Eng. Data*, 58(6):1425-1428, May 23, 2013.
(Continued)

*Primary Examiner* — Thuan D Dang
(74) *Attorney, Agent, or Firm* — Klarquist Sparkman, LLP

(57) ABSTRACT

Disclosed herein are embodiments of a method and system for converting ethanol to para-xylene. The method also provides a pathway to produce terephthalic acid from biomass-based feedstocks. In some embodiments, the disclosed method produces p-xylene with high selectivity over other aromatics typically produced in the conversion of ethanol to xylenes, such as m-xylene, ethyl benzene, benzene, toluene, and the like. And, in some embodiments, the method facilitates the ability to use ortho/para mixtures of methylbenzyaldehyde for preparing ortho/para xylene product mixtures that are amendable to fractionation to separate the para- and ortho-xylene products thereby providing a pure feedstock of para-xylene that can be used to form terephthalic anhydride and a pure feedstock of ortho-xylene that can be used for other purposes, such as phthalic anhydride.

23 Claims, 13 Drawing Sheets

(56) References Cited

U.S. PATENT DOCUMENTS

| | | | |
|---|---|---|---|
| 4,120,911 A | 10/1978 | Davidson | |
| 4,435,605 A * | 3/1984 | Butts | C07C 29/38 |
| | | | 568/705 |
| 4,701,562 A * | 10/1987 | Olson | C07C 45/002 |
| | | | 568/345 |
| 7,989,672 B2 | 8/2011 | Kinn et al. | |
| 8,263,372 B2 | 9/2012 | Oakley | |
| 8,507,228 B2 | 8/2013 | Simpson et al. | |
| 8,663,949 B2 | 3/2014 | Schultz | |
| 8,809,015 B2 | 8/2014 | Schultz et al. | |

OTHER PUBLICATIONS

Lusardi et al., "Identifying the roles of acid-base sites in formation pathways of tolualdehydes from acetaldehyde over MgO-based catalysts," *Catal. Sci. Technol.*, vol. 10, pp. 536-548, Dec. 16, 2019.

Moteki et al., "Formation Pathways toward 2- and 4-Methylbenzaldehyde via Sequential Reactions from Acetaldehyde over Hydroxyapatite Catalyst," *ChemCatChem*, 9(11):1921-1929, Apr. 28, 2017.

Selli et al., "Comparison between the surface acidity of solid catalysts determined by TPD and - 1IR analysis of pre-adsorbed pyridine," *Microporous and Mesoporous Materials*, 31 (1-2):129-140, Sep. 7, 1999.

Zhang et al., "Synthesis of $C_4$ and $C_8$ Chemicals from Ethanol on MgO Incorporated Faujasite Catalysts with Balanced Confinement Effects and Basicity," *ChemSusChem*, 9(7):736-748, Mar. 3, 2016.

\* cited by examiner

METHOD AND SYSTEM EMBODIMENTS FOR CONVERTING ETHANOL TO PARA-XYLENE AND ORTHO-XYLENE

ACKNOWLEDGMENT OF GOVERNMENT SUPPORT

This invention was made with Government support under Contract DE-AC05-76RL01830 awarded by the U.S. Department of Energy. The Government has certain rights in the invention.

FIELD

The present disclosure is directed to method embodiments for making para-xylene (or "p-xylene") and ortho-xylene (or "o-xylene") from ethanol, as well as system embodiments used for the method.

PARTIES TO JOINT RESEARCH AGREEMENT

The claimed invention arose under an agreement between Battelle Memorial Institute and LanzaTech, Inc., which agreement was in effect on or before the effective filing date of the claimed invention.

BACKGROUND

Terephthalic acid is a high volume and high market commodity chemical. It is one of the compounds used to make polyethylene terephthalate, known as PET, which is used for making beverage bottles, packaging films, and fibers. Terephthalic acid is currently made from the petroleum derived p-xylene produced from the naphtha reforming process. Potential unavailability of the petroleum-based p-xylene to meet the market demand and the end user's interest in sustainable PET products has created attention towards sustainable based feed source for the terephthalic acid production. Current ethanol-to-p-xylene processes either require an excessive number of catalytic steps, or produce p-xylene at low selectivity, thereby requiring capital-intensive separations. There exists a need in the art for a catalytic process using renewably sourced ethanol to provide polymer-grade p-xylene that can serve as the basis for the economical and renewable terephthalic acid production.

SUMMARY

Disclosed herein are embodiments of a method, comprising: contacting a feed stream comprising ethanol with an oxidation catalyst under oxidation conditions to form an oxidation zone effluent stream comprising acetaldehyde; passing the oxidation zone effluent stream to a dimerization zone and contacting the oxidation zone effluent stream with a dimerization catalyst under dimerization conditions to produce a dimerization zone effluent stream comprising 2-butenal; passing the dimerization zone effluent stream to a cyclization zone and contacting the dimerization zone effluent stream with a cyclization catalyst under cyclization conditions to form a cyclization zone effluent stream comprising o-methylbenzaldehyde and/or p-methylbenzaldehyde; and passing the cyclization zone effluent stream to a hydrogenation zone and contacting the cyclization zone effluent stream with a hydrogenation catalyst comprising a first Group VIII metal deposited on a support material to produce a hydrogenation zone effluent comprising a non-equilibrium mixture of xylenes.

Also disclosed herein are embodiments of an apparatus comprising: a gas fermentation bioreactor in fluid communication with an oxidation reactor; the oxidation reactor in fluid communication with a dimerization reactor; the dimerization reactor in fluid communication with a cyclization reactor; the cyclization reactor in fluid communication with a hydrogenation reactor; the hydrogenation reactor in fluid communication with a first fractionation zone; the first fractionation zone in fluid communication with a second fractionation zone; and the second fractionation zone in fluid communication with a first crystallizer.

The foregoing and other objects and features of the present disclosure will become more apparent from the following detailed description, which proceeds with reference to the accompanying figures.

DETAILED DESCRIPTION

I. Overview of Terms

Figure 1A:
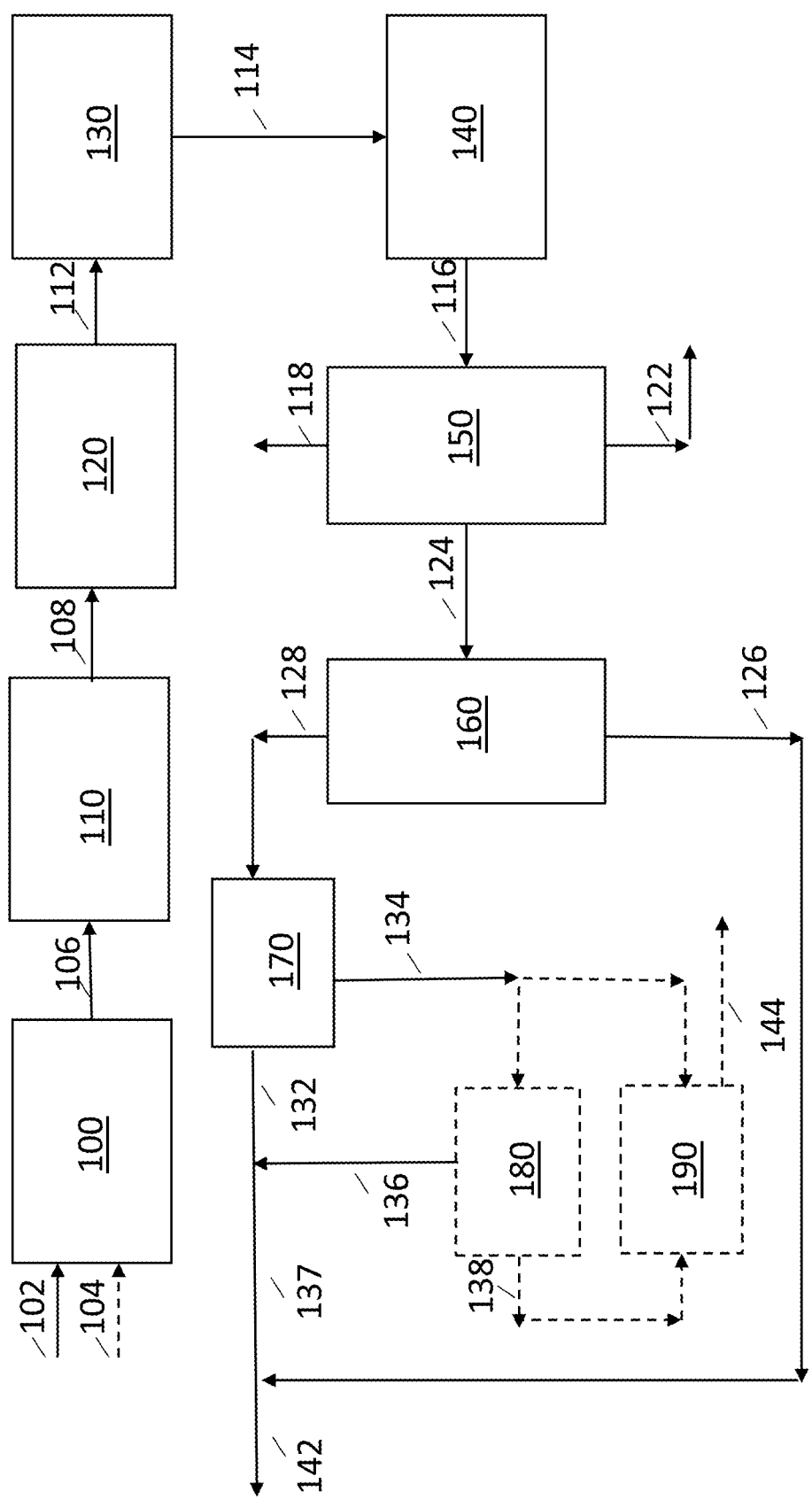
FIGS. 1A and 1B provide schematic diagrams outlining representative method embodiment steps and/or system components for converting ethanol to xylene compounds, such as o-xylene and p-xylene, wherein FIG. 1A summarizes steps and system components used in certain disclosed embodiments and FIG. 1B summarizes steps used in certain disclosed embodiments.

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, molecular weights, molarities, voltages, capacities, and so forth, as used in the specification or claims are to be understood as being modified by the term "about." Accordingly, unless otherwise implicitly or explicitly indicated, or unless the context is properly understood by a person of ordinary skill in the art to have a more definitive construction, the numerical parameters set forth are approximations that may depend on the desired properties sought and/or limits of detection under standard test conditions/methods as known to those of ordinary skill in the art. When directly and explicitly distinguishing embodiments from discussed prior art, the embodiment numbers are not approximates unless the word "about" is recited.

Although the operations of exemplary embodiments of the disclosed method may be described in a particular, sequential order for convenient presentation, it should be understood that disclosed embodiments can encompass an order of operations other than the particular, sequential order disclosed, unless the context dictates otherwise. For example, operations described sequentially may in some cases be rearranged or performed concurrently. Further, descriptions and disclosures provided in association with one particular embodiment are not limited to that embodiment and may be applied to any disclosed embodiment.

Although there are alternatives for various components, parameters, operating conditions, etc. set forth herein, that does not mean that those alternatives are necessarily equivalent and/or perform equally well. Nor does it mean that the alternatives are listed in a preferred order unless stated otherwise.

In order to facilitate review of the various embodiments of the disclosure, the following explanations of specific terms are provided:

Cyclization Catalyst: A catalyst that is capable of promoting 2-butenal condensation and cyclization to o-methylbenzaldehyde and/or p-methylbenzaldehyde.

Cyclization Conditions: Reaction conditions, such as temperature, pressure, reaction time, weight hourly space velocity, and/or cyclization catalyst loading that can be controlled and/or modified to facilitate 2-butenal condensation and cyclization to o-methylbenzaldehyde and/or p-methylbenzaldehyde.

Cyclization Zone: A reaction zone comprising system components configured to contact a dimerization zone effluent stream comprising 2-butenal with a cyclization catalyst to form a cyclization zone effluent stream comprising o-methylbenzaldehyde and/or p-methylbenzaldehyde Dimerization Catalyst: A catalyst that is capable of promoting acetaldehyde dimerization to 2-butenal.

Dimerization Conditions: Reaction conditions, such as temperature, pressure, reaction time, weight hourly space velocity, and/or dimerization catalyst loading that can be controlled and/or modified to facilitate acetaldehyde dimerization to 2-butenal.

Dimerization Zone: A reaction zone comprising system components configured to contact an oxidation zone effluent stream comprising acetaldehyde with a dimerization catalyst to form a dimerization zone effluent stream comprising 2-butenal.

Feed Stream: A fluid stream that is passed to one or more zones. An exemplary feed stream is a fluid stream comprising ethanol that can be introduced into an oxidation zone.

Fractionization Zone: A zone comprising system components capable of fractionating one fluid component from another (e.g., fractionating p-xylene from o-xylene).

Hydrogenation Catalyst: A catalyst that is capable of promoting o-methylbenzaldehyde and/or p-methylbenzaldehyde hydrogenation to a xylene product mixture, wherein the xylene product mixture comprises o-xylene and/or p-xylene. In particular embodiments, the xylene product mixture is a non-equilibrium mixture of xylenes.

Hydrogenation Conditions: Reaction conditions, such as temperature, pressure, reaction time, and/or hydrogenation catalyst loading that can be controlled and/or modified to facilitate hydrogenation of o-methylbenzaldehyde to o-xylene and/or p-methylbenzaldehyde to p-xylene.

Hydrogenation Zone: A reaction zone comprising system components configured to contact a cyclization zone effluent stream comprising o-methylbenzaldehyde and/or p-methylbenzaldehyde with a hydrogenation catalyst to form an effluent stream comprising a xylene product mixture. In particular embodiments, the xylene product mixture is a non-equilibrium mixture of xylenes.

Non-Equilibrium Mixture of Xylenes: A mixture of xylene compounds, wherein the mixture comprises p-xylene, o-xylene, and mete-xylene (or "m-xylene", wherein the concentration of any m-xylene in the mixture is less than 50 wt % of a m-xylene equilibrium concentration. The mixture of xylenes is exclusive of other compounds containing eight (8) carbon atoms.

Oxidation Catalyst: A catalyst that is used to promote converting ethanol to acetaldehyde.

Oxidation Conditions: Reaction conditions, such as temperature, pressure, reaction time, and/or oxidation catalyst loading that can be controlled and/or modified to facilitate converting ethanol to acetaldehyde.

Oxidation Zone: A reaction zone comprising system components configured to contact a feed stream comprising ethanol with an oxidation catalyst to form an oxidation zone effluent stream comprising acetaldehyde.

II. Introduction

Polymer-grade p-xylene is a valuable product in various industries such as the production of terephthalic acid, which in turn is used to produce various polymers. Polymer-grade p-xylene used in these industries needs to have a purity of at least 99.95 mass % p-xylene, or at least 99.97 (or greater) mass % p-xylene. Current processes which yield high purity p-xylene with sufficient commercial yield require substantial investment in purification and isomerization operations including vessels, recycle of effluent streams, and utilities, all of which have high capital and operating expenditures. Further, methods that exist in the art to produce terephthalic acid from ethanol rely on oxidizing a para-methylbenzaldehyde product formed during the process to the terephthalic acid. Such methods typically require focusing on the ability to increase the amount of para-methylbenzaldehyde produced in the process in order to arrive at a sufficient amount of the material to be oxidized to the terephthalic acid. This can typically require using expensive catalysts and/or processing parameters that do not lend to industrial usage.

The disclosure herein provides embodiments of a method to provide high purity p-xylene, such as polymer-grade p-xylene, without the need for isomerizing large amounts of undesired xylene products, such as m-xylene, and subsequent recycling. Additionally, the disclosure describes method embodiments that use separation techniques, such as crystallization, which is less costly as compared to adsorptive separation. Furthermore, the disclosed method embodiments are compatible with unconventional feedstocks, such as ethanol, which may be derived from a sustainable source. In some embodiments, the sustainable source of ethanol may be industrial waste gases, such as steel mill gas, or syngas from various sources such as gasification of biomass or municipal/industrial waste. In some embodiments the sustainable source of ethanol may be a gas comprising $CO_2$.

In particular embodiments, a method for making p-xylene from ethanol is disclosed, which provides a novel method for producing p-xylene, including polymer-grade p-xylene, and, in some embodiments, terephthalic acid from sustainable-based feedstocks. In some embodiments, the disclosed method produces p-xylene with high selectivity over other aromatics, such as m-xylene, ethyl benzene, benzene, toluene, and the like. The disclosed method is more efficient and more economical than conventional methods. Also, the method can produce mixtures of o-xylene and p-xylene from methylbenzyaldehyde that can be fractionated to separate the p- and o-xylene products, thereby providing a stream highly enriched in p-xylene. This stream can be introduced to an additional purification process to economically produce polymer-grade p-xylene and an enriched stream of o-xylene that can be used for other purposes, such as phthalic anhydride production. Parameters of the novel method (e.g., reagents and/or reaction conditions) can be controlled to provide p/o methylbenzaldehyde mixtures and p/o-xylene product mixtures that include little to no undesired products, such as undesired aromatics (e.g., m-xylene, toluene, or benzene), and/or saturated cyclic products (e.g., dimethylcyclohexane). These are just a few of the improvements that can be achieved using the method embodiments disclosed herein.

III. Method Embodiments

The present disclosure describes embodiments of a method for producing p-xylene from ethanol. Ethanol used in the disclosed method can be obtained from petroleum-derived ethanol from ethylene, or ethanol derived from a sustainable source, such as industrial waste or off gases, such as steel mill gas, syngas from various sources (e.g., gasification of biomass or municipal/industrial waste), or gas comprising $CO_2$. In some embodiments, p-xylene produced using the disclosed method can be used to produce terephthalic acid. In yet some additional embodiments, o-xylene produced by the method can be further converted to phthalic anhydride.

In particular embodiments of the method, a feed stream comprising ethanol and, optionally, an oxygen stream or a stream containing a source of oxygen, is contacted with an oxidation catalyst under oxidation conditions in an oxidation zone to form an effluent stream comprising acetaldehyde. The oxidation zone can comprise a reactor or vessel that contains the oxidation catalyst. Alternatively, the oxidation zone can be one section of a reactor or vessel. If the oxidation zone is one section of a reactor, the reactor may comprise one or more reaction zones as described hereinafter. The oxidation catalyst can be present in the reactor as a stationary bed through which the feed stream is flowed through or it can be present as a moving bed or as particulates that are fluidized and flowed co-currently or counter currently with the feed stream. The vessel or reactor can comprise one or more inlets for introducing the reactants and one or more outlets for removing the products and unreacted reactants. In some embodiments, the ethanol is mixed with air and contacted with the catalyst at a temperature ranging from 500° C. to 650° C. One oxidation process known as Verb Chemie Process involves mixing ethanol with air prior to introducing the mixture into the oxidation vessel or zone or the ethanol and air can be introduced as separate streams into the oxidation zone/vessel. Such a process can be used in the current method. In some embodiments, the acetaldehyde can be formed from ethanol by dehydrogenation processes. Such processes will utilize catalysts comprising a metal oxide or carbon support material or zeolite material and a metal or metals selected from Cu, Au, Ni, Zn, Mn, Co, V, Ag, Fe, Ce, or Cr. In particular embodiments, the catalyst is selected from a catalyst comprising copper and chromium and either a mesoporous carbon support material or a $Al_2O_3$ support material.

The feed stream for the oxidation zone can comprise ethanol that is derived from C1 gas fermentation of a source material. The fermentation can use the source material directly such as in the fermentation of cellulosic material, or indirectly such as through the gasification of biomass to produce syngas. Examples of source material include cellulosic material, sugars, industrial process waste gas or non-waste gas, combustion engine exhaust fumes, such as automobile exhaust fumes, biogas, landfill gas, direct air capture, from electrolysis or combinations thereof. The substrate and/or C1-carbon source of the gas fermentation to generate the ethanol feed stream may be syngas generated by pyrolysis, torrefaction, or gasification. In other words, carbon in waste material may be recycled by pyrolysis, torrefaction, or gasification to generate syngas which is used as the substrate and/or C1-carbon source in the gas fermentation that generates the ethanol feed stream. The substrate and/or C1-carbon source in the gas fermentation may be a gas stream comprising methane.

In particular embodiments, the feed stream can comprise ethanol derived from waste gas produced by an industrial process selected from ferrous metal products manufacturing, steel mill manufacturing, non-ferrous products manufacturing, petroleum refining, electric power production, carbon black production, paper and pulp production, ammonia production, methanol production, coke manufacturing, petrochemical production, carbohydrate fermentation, cellulosic fermentation, cement making, aerobic digestion, anerobic digestion, catalytic processes, natural gas extraction, oil extraction, geological reservoirs, gas from fossil resources such as natural gas coal and oil, or any combination thereof. Examples of specific processing steps within an industrial process include catalyst regeneration, fluid catalyst cracking, and catalyst regeneration. Air separation and direct air capture are other suitable industrial processes. In these embodiments, the substrate and/or C1-carbon source for the gas fermentation to generate the ethanol in the feed stream may be captured from the industrial process before it is emitted into the atmosphere, using any known method.

In yet some additional embodiments, the feed stream can comprise ethanol derived from synthesis gas, known as syngas, which may be obtained from pyrolysis, torrefaction, reforming, partial oxidation, or gasification processes. Examples of gasification processes include gasification of coal, gasification of refinery residues, gasification of petroleum coke, gasification of biomass, gasification of lignocellulosic material, gasification of waste wood, gasification of black liquor, gasification of municipal solid waste, gasification of municipal liquid waste, gasification of industrial solid waste, gasification of industrial liquid waste, gasification of refuse derived fuel, gasification of sewerage, gasification of sewerage sludge, gasification of sludge from wastewater treatment, gasification of biogas. Examples of reforming processes include, steam methane reforming, steam naphtha reforming, reforming of natural gas, reforming of biogas, reforming of landfill gas, naphtha reforming, and dry methane reforming. Examples of partial oxidation processes include thermal and catalytic partial oxidation processes, catalytic partial oxidation of natural gas, partial oxidation of hydrocarbons. Examples of municipal solid waste include tires, plastics, fibers, such as in shoes, apparel, and textiles. Municipal solid waste may be simply landfill-type waste. The municipal solid waste may be sorted or unsorted. Examples of biomass may include lignocellulosic material and may also include microbial biomass. Lignocellulosic material may include agriculture waste and forest waste.

The substrate and/or C1-carbon source may be a gas stream comprising methane. Such a methane containing gas may be obtained from fossil methane emission such as during fracking, wastewater treatment, livestock, agriculture, and municipal solid waste landfills. It is also envisioned that the methane may be burned to produce electricity or heat, and the C1 byproducts may be used as the substrate or carbon source.

The fermentation of gaseous stream comprising C1 compounds (e.g., CO, $CO_2$, $Ch_4$, $CH_3OH$, etc.) to produce products such as ethanol and acetic acid are well known in the art. The fermentation process comprises contacting a gaseous C1-containing stream with a at least one C1-fixing bacteria in a liquid medium in a bioreactor. In one embodiment, the bacteria can be selected from the genus Clostridia. Exemplary fermentation processes are described in U.S. Pat. Nos. 8,507,228; 8,263,372; 8,809,015; and 8,663,949, the relevant portions of which are incorporated herein by reference.

As discussed above, in some embodiments, the feed stream may comprise ethanol that is derived from liquid fermentation of sugars and or cellulosic material. In yet additional embodiments, the feed stream may comprise ethanol from hydration of ethylene. The ethanol may also be produced from traditional ethanol manufacturing processes, or in other words, ethanol from a source other than cellulosic material, sugar, industrial process waste gas, automobile exhaust fumes, or syngas from gasification operations. In particular embodiments, the oxidation zone can convert at least 20 wt % of the ethanol of the feed stream to acetaldehyde, such as 20 wt % to 95 wt % of the ethanol, or 50 wt % to 90 wt % of the ethanol, or 70 wt % to 90 wt % of the ethanol. The oxidation zone operates at temperatures from 200° C. to 500° C. In particular embodiments, the oxidation zone operates 250° C. to 400° C. In some embodiments, the oxidation zone can be operated under suitable pressures, which are recognized by those of ordinary skill in the art with the benefit of the present disclosure.

The effluent stream from the oxidation zone comprising acetaldehyde is next contacted with a dimerization catalyst to produce an effluent stream comprising 2-butenal. This further involves passing the effluent stream comprising acetaldehyde from the oxidation zone to the dimerization zone. The dimerization zone can comprise a separate reactor or vessel, or a separate section of the reactor or vessel, that houses the oxidation zone. The dimerization catalyst can be present in the reactor as a stationary bed through which the acetaldehyde stream is flowed through or can be present as particulates that are fluidized and flowed co-currently or counter currently with the acetaldehyde stream. The vessel or reactor can comprise one or more inlets for introducing the reactants and one or more outlets for removing the products and unreacted reactants. If the dimerization zone is housed in the same reactor or vessel as the oxidation zone, then the effluent from the oxidation zone can be passed directly to the dimerization zone. The dimerization zone is operated under dimerization conditions. Dimerization conditions can comprise a reaction temperature ranging from 150° C. to 310° C., such as 160° C. to 300° C., or 180° C. to 300° C. and can be conducted at pressures ranging from 689.5 kPa (100 psig) to 1034 kPa (150 psig), such as 689.5 kPa (100 psig), 758 kPa (110 psig), or 1034 kPa (150 psig). In some embodiments, the dimerization catalyst is a catalyst that comprises an oxide material, such as MnO, MgO, ZnO, $ZrO_2$, $TiO_2$, or any combination thereof. In some embodiments, the catalyst can further comprise a support material, such as an alumina support (e.g., $Al_2O_3$). In particular embodiments, the catalyst is selected from MnO—ZnO—$ZrO_2$, MgO—$Al_2O_3$, ZnO—$ZrO_2$ (10:1), ZnO—$ZrO_2$ (2:1), or $TiO_2$. In particular embodiments, the dimerization zone can convert at least 15 wt % of the acetaldehyde of the effluent produced by the oxidation zone to a product mixture comprising 2-butenal, such as 15 wt % to 65 wt % or higher of the acetaldehyde, or 20 wt % to 65 wt % of the acetaldehyde, or 32 wt % to 65 wt %, or 59 wt % to 65 wt % or higher of the acetaldehyde. In some embodiments, 58 wt % or more of the product mixture can be 2-butenal, such as 68 wt % to 91 wt %, or 77 wt % to 91 wt %, or 81 wt % to 91 wt %, or 84 wt % to 91 wt %, or 88 wt % to 91 wt %.

In some embodiments, exposing the effluent stream comprising 2-butenal to a cyclization catalyst to produce an effluent stream comprising a mixture of o-methylbenzaldehyde and/or p-methylbenzaldehyde can comprise contacting the effluent stream comprising the 2-butenal with the cyclization catalyst in a cyclization zone. This further involves passing the effluent stream comprising 2-butenal from the dimerization zone to a cyclization zone. The cyclization zone can comprise a separate reactor or vessel, or a separate section of the reactor or vessel, that houses the dimerization zone or the oxidation zone plus the dimerization zone. The cyclization catalyst can be present in the reactor as a stationary bed through which the 2-butenal stream is flowed through, or can be present as particulates that are fluidized and flowed co-currently or counter currently with the acetaldehyde stream. The vessel or reactor can comprise one or more inlets for introducing the reactants and one or more outlets for removing the products and unreacted reactants. If the cyclization zone is housed in the same reactor or vessel as the dimerization zone, then the effluent from the dimerization zone can be passed directly to the cyclization zone. The cyclization zone can be operated under cyclization conditions. Cyclization conditions can comprise using a reaction temperature ranging from 250° C. or higher, such as 250° C. to 350° C., or 250° C. to 325° C., or 275° C. to 300° C. In particular embodiments, the cyclization step is performed at pressures ranging from atmospheric pressure 101.35 kPa (14.7 psig) to 1034 kPa (150 psig), such as atmospheric pressure to 689.5 kPa (100 psig). In some embodiments, a weight hourly space velocity (or "WHSV") ranging from 0.2 $h^{-1}$ to 0.25 $h^{-1}$, such as 0.2 $h^{-1}$ to 0.23 $h^{-1}$, or 0.2 $h^{-1}$ to 0.22 $h^{-1}$ is used. In particular embodiments, the cyclization zone can be operated at 150° C. and 689.5 kPa (100 psig), or at 260° C. and 101.35 kPa (14.7 psig), or at 175° C. and 1034 kPa (150 psig), or at 200° C. and 1034 kPa (150 psig), or at 300° C. and 101.35 kPa (14.7 psig).

In some embodiments, the cyclization catalyst is a metal oxide catalyst, such as a metal oxide catalyst comprising a Group IV metal (also known as Group 4 under the new IUPAC classification), such as Ti or Zr; or a Group II metal (also known as Group 2 under the new IUPAC classification), such as Mg. In some independent embodiments, the cyclization catalyst can further comprise a solid support, such as an alumina support (e.g., $Al_2O_3$), SrO, CaO, MgO, $La_2O_3$, $SiO_2$, $SiO_2$—$Al_2O_3$, $TiO_2$—$Al_2O_3$, or a zeolite support such as H-Mordenite, or Faujasite, onto which the desired metal oxide is dispersed or deposited. In some embodiments, the cyclization catalyst is selected from $TiO_2$ or a hydrotalcite catalyst comprising MgO and $Al_2O_3$. In particular embodiments, the hydrotalcite catalyst can have a formula of $Mg_xAl_y$, wherein "Mg" represents MgO, "Al" represents $Al_2O_3$, x ranges from 1 to 4, and y typically is 1. In some such embodiments, the hydrotalcite catalyst can be $Mg_2Al_1$, $Mg_3Al_1$, or $Mg_4Al_1$. In some embodiments, the hydrotalcite catalyst can be modified to comprise an alkali metal, such as Na or K. The amount of alkali metal included in the catalyst can range from greater than 0 wt % to 20 wt % or higher, such as greater than 0 wt % to 20 wt %, or greater than 0 wt % to 10 wt %, or greater than 0 wt % to 5 wt %. In particular embodiments, the catalyst used in the cyclization zone can be selected from $TiO_2$; $Mg_4Al_1$; $Mg_3Al_1$; $Mg_2Al_1$; $Mg_4Al_1$ comprising 5 wt % or 10 wt % or 20 wt % Na; or $Mg_4Al_1$ comprising 5 wt % K. In particular embodiments, the cyclization zone can convert at least 50 wt % of the 2-butenal of the effluent produced by the dimerization zone to a resulting product mixture comprising o-methylbenzaldehyde and p-methylbenzaldehyde, such as 50 wt % to 95 wt % or higher of the 2-butenal, or 75 wt % to 95 wt % of the 2-butenal, or 80 wt % to 95 wt % of the 2-butenal. In particular embodiments, the dimerization step provides a product mixture comprising o-methylbenzaldehyde and p-methylbenzaldehyde but no meta-methylbenzaldehyde (or "m-methylbenzaldehyde"). In some such embodiments, the reaction mixture may comprise trace amounts (e.g., less than 20 wt % total) of other compounds, such as higher aldehydes (e.g., 2,4,6-octatrienal), benzaldehyde, or hydrogenated products. In some embodiments, the reaction mixture may only comprise other compounds (e.g., higher aldehydes, benzaldehyde, and/or hydrogenated products) in an amount ranging from greater than 0% to 20%, greater than 0% to 15%, or greater than 0% to 10% of the reaction mixture.

In some embodiments, the effluent stream comprising o-methylbenzaldehyde and/or p-methylbenzaldehyde is contacted with a hydrogenation catalyst in a hydrogenation zone to produce an effluent comprising a xylene product mixture. This involves passing the effluent stream comprising the o-methylbenzaldehyde and/or p-methylbenzaldehyde mixture from the cyclization zone to the hydrogenation zone. The hydrogenation zone comprises a reactor or vessel in which the hydrogenation catalyst is contained. In particular embodiments, the hydrogenation zone comprises a reactor vessel suitable for flow-based processing) comprising one or more inlets and outlets and that is configured to contain the catalyst. The hydrogenation zone can comprise a separate reactor or vessel, or a separate section of the reactor or vessel, that houses the hydrogenation zone or any or all of the previous zones plus the hydrogenation zone. The hydrogenation catalyst can be present in the reactor as a stationary bed through which the cyclization zone effluent stream is flowed through or can be present as particulates that are fluidized and flowed co-currently or counter currently with the cyclization zone effluent stream. The vessel or reactor can comprise one or more inlets for introducing the reactants and one or more outlets for removing the products and unreacted reactants. If the hydrogenation zone is housed in the same reactor or vessel as the cyclization zone, then the effluent from the cyclization zone can be passed directly to the hydrogenation zone. The hydrogenation zone can be operated under hydrogenation conditions. Hydrogenation conditions can comprise operating the hydrogenation zone at temperatures ranging from greater than 100° C. to less than 200° C., such as 110° C. to 190° C., or 120° C. to 180° C., or 125° C. to 175° C. In particular embodiments, the temperature is 125° C., 130° C., 140° C., 150° C., 160° C., 170° C., or 180° C., or any temperatures between 125° C. and 180° C. In some embodiments, hydrogenation conditions can comprise operating the hydrogenation zone at pressures ranging from greater than 344.7 kPa (50 psig) to less than 1378.9 kPa (2000 psig), such as 689.5 kPa (100 psig) to 10342 kPa (1500 psig), or 1378.9 kPa (200 psig) to 6894.7 kPa (1000 psig), or 3447.4 kPa (500 psig) to 5515.8 kPa (800 psig). In particular embodiments, the pressure is 689.5 kPa (100 psig), 1034 kPa (150 psig), 1378.9 kPa (200 psig), 1723.7 kPa (250 psig), 2068.4 kPa (300 psig), 2413.2 kPa (350 psig), 2757.9 kPa (400 psig), 3102.6 kPa (450 psig), 3447.4 kPa (500 psig), 3792 kPa (550 psig), 4136.8 kPa (600 psig), 4481.6 kPa (650 psig), 4826.3 kPa (700 psig), 5171.1 kPa (750 psig), 5515.8 kPa (800 psig), 5860.5 kPa (850 psig), 6205.3 kPa (900 psig), 6550 kPa (950 psig), or 6894.7 kPa (1000 psig). In particular embodiments, the hydrogenation zone is operated at 125° C. and 689.5 kPa (100 psig), 150° C. and 3447.4 kPa (500 psig), at 150° C. and 6894.7 kPa (1000 psig), or 180° C. and 6894.7 kPa (1000 psig). In particular embodiments, the hydrogenation zone is operated at temperatures ranging from 125° C. to 175° C. or lower and at pressures ranging from 689.5 kPa (100 psig) to 5515.8 kPa (800 psig) or less.

In some embodiments, hydrogenation conditions can comprise operating the hydrogenation zone at any of the above temperatures and/or pressures for a time period sufficient to convert all, or substantially all, of the o-methylbenzaldehyde and/or p-methylbenzaldehyde to the corresponding xylene product mixture. In such embodiments, "substantially all" means at least 90 wt %, such as at least 93 wt %, or at least 94 wt %, or at least 95 wt %, or at least 96 wt %, or at least 97 wt %, or at least 98 wt %, or at least 99 wt % of the effluent comprising the o-methylbenzaldehyde and/or p-methylbenzaldehyde. In some embodiments, the time period ranges from minutes to an amount of time whereby the process is stopped or the catalyst efficiency decreases by 50%. In some embodiments, the time period can range from 30 minutes to 600 hours or more, such as 1 hour to 600 hours (or more), or 3 hours to 600 hours (or more), or 6 hours to 600 hours (or more). In particular embodiments, the time period can be 30 minutes, 1 hour, 6 hours, 400 hours, and 600 hours. In particular embodiments, the hydrogenation zone can convert at least 85 wt % of the mixture of the o-methylbenzaldehyde and p-methylbenzaldehyde of the effluent produced by the cyclization zone to the xylene product mixture, such as 85 wt % to 100 wt % of the mixture of the o-methylbenzaldehyde and p-methylbenzaldehyde, or 90 wt % to 100 wt % of the mixture of the o-methylbenzaldehyde and p-methylbenzaldehyde, or 95 wt % to 100 wt % of the mixture of the o-methylbenzaldehyde and p-methylbenzaldehyde.

In some embodiments, the hydrogenation catalyst comprises a Group VIII (also known as Group 8, 9, or 10 under the new IUPAC classification) metal and a support material. In particular embodiments, the Group VIII metal of the hydrogenation catalyst is selected from iron, ruthenium, cobalt, rhodium, iridium, nickel, palladium, platinum, or combinations thereof. In particular embodiments, the Group VIII metal is palladium, platinum, or ruthenium. In representative embodiments, the Group VIII metal is palladium. The support material of the hydrogenation catalyst can be selected from carbon, silicas, aluminas, silica-aluminas, titania, zirconia, zeolites, zinc oxides, or combinations thereof. In particular embodiments, the support material is a carbon material, a silica, an alumina (e.g., $Al_2O_3$), a titania (e.g., $TiO_2$), a zirconia (e.g., $ZrO_2$), a niobium oxide (e.g., $Nb_2O_5$), a low acidity zeolite (e.g., ZSM-5), or a carbon support (a carbon support selected from a carbon support sold under the tradenames Nuchar® sold by Ingevity, a Hyperion 07C or Hyperion 02C support sold by Hyperion Catalysis International, ROX HF or DARCO®-LS supports sold by Cabot Norit, a carbon support sold by Jacobi, CECA, or PICA). The Group VIII metal typically is deposited on the support material by means known to those in the art and with the benefit of the present disclosure and exists in metallic form on the support under reaction conditions disclosed herein. In particular embodiments, the support material is carbon, $Al_2O_3$, $TiO_2$, or $ZrO_2$. In some embodiments, the support material can be substantially non-acidic. Acidity of the support material can be measured by determining the surface concentration of acid sites of the support material using Fourier transform infra-red (FTIR) analysis of adsorbed pyridine. The amount of the Group VIII metal used in the catalyst, expressed as the amount of metal per total weight of the catalyst, can range from 0.1 wt % to 3 wt %, such as 0.5 wt % to 2.5 wt %, or 0.75 wt % to 2 wt %, or 1 wt % to 2 wt %. In some embodiments, the amount of the Group VIII metal used can range from 0.75 wt % to 3 wt %, such as 1.5 wt % to 3 wt % per total weight of the catalyst. In some other embodiments, the amount of the Group VIII metal used can range from greater than 0 wt % to less than 0.75 wt %, such as greater than 0 wt % to 0.5 wt %, or greater than 0 wt % to 0.25 wt %, or greater than 0 wt % to 0.2 wt %, or greater than 0 wt % to 0.15 wt %, or greater than 0 wt % to 0.1 wt % per total weight of the catalyst. In particular embodiments, the amount of the Group VIII metal can be used in an amount selected from 0.1 wt %, 0.25 wt %, 0.5 wt %, 0.75 wt %, 1.5 wt %, or 3 wt % per total weight of the catalyst. In an independent embodiment, the hydrogenation catalyst comprises Rainey nickel, without a support material.

In some embodiments, the hydrogenation catalyst can further comprise a modifier component. The modifier component can be an element, typically a metal, that is used in combination with a metal catalyst to modify properties of the catalyst. In some embodiments, the modifier component can facilitate stabilizing the metal catalyst and/or reducing acidic sites on a support material. In particular embodiments, the modifier component is a metal that is deposited on the support of the hydrogenation catalyst. In some embodiments, the modifier component can comprise a Group VII metal (also known as Group 7 under the new IUPAC classification), or a Group IV metal (also known as Group 14 under the new IUPAC classification), a Group I metal (also known as Group 1 under the new IUPAC classification and/or as an alkali metal), a Group II metal (also known as Group 2 under the new IUPAC classification and/or as an alkaline earth metal), or a combination thereof. In particular embodiments, the modifier component can comprise rhenium, tin, or combinations thereof. The amount of the modifier component used in the catalyst, expressed as the amount of metal per total weight of catalyst, can range from 0 wt % to 6 wt %, such as 0.1 wt % to 6 wt %, or 0.2 wt % to 4 wt %, or 0.5 wt % to 3 wt %, or 1.5 wt % to 2 wt %. In some embodiments, the amount of the modifier component used in the catalyst can range from 3 wt % to 6 wt %, such as 5 wt % to 6 wt %, expressed as the amount of modifier component per total catalyst. In some other embodiments, the amount of the modifier component used in the catalyst can range from 0.1 wt % to 1 wt % such as 0.1 wt % to 0.5 wt %, or 0.1 wt % to 0.2 wt % expressed as the amount of modifier component per total catalyst. In particular embodiments, the amount of the modifier component present on the catalyst is selected from 0.1 wt %, 0.2 wt %, 0.5 wt %, 1 wt %, 1.5 wt %, 5 wt %, or 6 wt %, expressed as the amount of modifier component per total catalyst. In particular embodiments, the hydrogenation zone can further comprise a solvent. In some embodiments, the solvent can be hydrocarbon solvent, such as dodecane, decane, and dioxane.

In representative embodiments, the hydrogenation catalyst comprises the Group VIII metal, the support, and the modifier component. In yet other embodiments, the hydrogenation catalyst comprises the Group VIII metal and the support. In particular embodiments, the hydrogenation catalyst consists of the Group VIII metal and the support. In yet additional particular embodiments, the hydrogenation catalyst consists of the Group VIII metal, the support, and the modifier component. In an independent embodiment, the hydrogenation catalyst consists of Rainey nickel. The components of the hydrogenation catalyst may be added sequentially in any order, or in any combination, including all together at the same time. In representative embodiments, the hydrogenation catalyst comprises palladium, a carbon material, and rhenium; or, palladium, $Al_2O_3$, and rhenium; or palladium, $TiO_2$, and rhenium; or palladium, $ZrO_2$, and rhenium; platinum, a carbon material, and rhenium; or, platinum, $Al_2O_3$, and rhenium; or platinum, $TiO_2$, and rhenium; or platinum, $ZrO_2$, and rhenium; or ruthenium, a carbon material, and rhenium; or, ruthenium, $Al_2O_3$, and rhenium; or ruthenium, $TiO_2$, and rhenium; or ruthenium, $ZrO_2$, and rhenium. In yet other representative embodiments, the hydrogenation catalyst comprises palladium and $Al_2O_3$; or palladium and $ZrO_2$; or palladium and $TiO_2$, or palladium and carbon; or platinum and $Al_2O_3$; or platinum and $ZrO_2$; or platinum and $TiO_2$, or platinum and carbon; or ruthenium and $Al_2O_3$; or ruthenium and $ZrO_2$; or ruthenium and $TiO_2$, or ruthenium and carbon. In some embodiments, the method can comprise using 0.1 wt % to 3 w % of the catalyst. In particular embodiments, such amounts correspond to (i) the total amount of the Group VIII metal, the support material, and any modifier component, if present, and is relative to the feed; or (ii) the total amount of the metal relative to the feed, such as in embodiments using Rainey nickel without a support material. In particular embodiments, 2 wt % of the catalyst is used. In particular representative embodiments, the hydrogenation catalyst comprises a mixture of 3 wt % Pd and 6 wt % Re on a carbon support material. In yet other embodiments, the hydrogenation catalyst comprises 1.5 wt % Pd and 3 wt % Re on a carbon support material; or 0.5 wt % Pd and 1 wt % Re on a carbon support material; or 0.1 wt % Pd and 2 wt % Re on a carbon support material; or 0.25 wt % Pd and 0.5 wt % Re on a carbon support material; or 0.25 wt % Pd and 0.5 wt % Re on a carbon support material; or 0.25 wt % Pd and 1.5 wt % Re on a carbon support material; or 0.25 wt % Pd and 6 wt % Re on a carbon support material; or 0.1 wt % Pd and 0.5 wt % Re on a carbon support material; or 0.1 wt % Pd and 1.5 wt % Re on a carbon support material; or 0.1 wt % Pd and 6 wt % Re on a carbon support material; or 0.75 wt % Pd and 5 wt % Re on a carbon support material; or 3 wt % Pd and 6 wt % Re on $Al_2O_3$; or 1.5 wt % Pd and 3 wt % Re on $Al_2O_3$; or 0.75 wt % Pd and 5 wt % Re on $Al_2O_3$; or 1.5 wt % Pd on $Al_2O_3$; or 1.5 wt % Pd on $ZrO_2$; or 0.25 wt % Pd on a carbon material.

In some particular embodiments, the xylene product mixture in the hydrogenation zone effluent comprises at least 85 wt % of a mixture comprising o-xylene and/or p-xylene. The balance of the xylene product mixture in the hydrogenation zone effluent may include toluene, benzene, m-xylene, ethylbenzene, and/or saturated aromatic compounds, such as dimethylcyclohexane. The hydrogenation zone effluent typically does not comprise an equilibrium amount of ethylbenzene. In some particular embodiments, the xylene product mixture consists essentially of o-xylene and p-xylene, wherein consisting essentially of means that the xylene product mixture is substantially free of an isomerized version of o-xylene and/or p-xylene (e.g., m-xylene), a saturated aromatic compound (e.g., dimethylcyclohexane), and/or cracked aromatic compounds (e.g., toluene or benzene) such that the amount of any such products, individually, is less than 15 wt %; or such that the amount of any such products, in total, is less than 30 wt %. Amounts of components present in the hydrogenation zone effluent can be determined using standardized techniques and methods recognizable by those of skill in the art with the benefit of the present disclosure. One exemplary method is gas chromatography coupled with flame ionization detection calibrated with external standards, with compounds being identified by mass spectroscopy. In some embodiments, the xylene product mixture can comprise o-xylene and/or p-xylene, and substantially no m-xylene. In an independent embodiment, the xylene product mixture consists of o-xylene and p-xylene.

In some embodiments, the xylene product mixture comprises p-xylene at a concentration ranging from 65 wt % to 100 wt %, such as at least 65 wt %, or at least 75 wt %, or at least 85 wt %. In such embodiments, any remaining weight balance can be o-xylenes or a mixture of o-xylenes and trace amounts (e.g., less than 5 wt % total) of other aromatics (e.g., m-xylene, benzene, or toluene) or a saturated aromatic (e.g., dimethylcyclohexane). In some embodiments, the p-xylene concentration ranges from 65 wt % to 99 wt %, or 70 wt % to 99 wt %, or 75 wt % to 99 wt %, or 80 wt % to 99 wt %, or 85 wt % to 99 wt %. In some other embodiments, the xylene product mixture comprises o-xylene, p-xylene, and m-xylene. In such embodiments, the xylene product mixture comprises a non-equilibrium mixture of the three different xylene products. In such non-equilibrium mixtures, m-xylenes is present at a concentration lower than 50 wt % of a m-xylene equilibrium concentration. In some embodiments, if any isomerization to m-methylbenzaldehyde takes place and any such m-methylbenzaldehyde is converted to m-xylenes, the resulting amount of m-xylenes is less than 50% of a m-xylene equilibrium concentration. In some embodiments, if m-xylene is present, it is present at a concentration ranging from greater than 0 wt % up to 49 wt % of a m-xylene equilibrium concentration, such as greater than 0 wt % up to 45 wt %, or greater than 0 wt % to 40 wt %, or greater than 0 wt % to 35 wt %, greater than 0 wt % to 30 wt %, greater than 0 wt % to 20 wt %, greater than 0 wt % to 10 wt %, greater than 0 wt % to 5 wt %, or greater than 0 wt % to 1 wt % of a m-xylene equilibrium concentration.

In some embodiments, the method can further comprise converting the purified p-xylene to terephthalic acid. The purified p-xylene can be converted to terephthalic acid under oxidative conditions that would be recognized by those of skill in the art with the benefit of the present disclosure. In some embodiments, this conversion can be conducted in air using acetic acid with a manganese or cobalt acetate catalyst. In yet additional embodiments, the method can further comprise converting the terephthalic acid to Polyethylene Terephthalate (PET). In such embodiments, the method can comprise combining the terephthalic acid with ethylene glycol in an esterification reactor or vessel, which can be operated under conditions known to those of skill in the art with the benefit of the present disclosure, such as at pressures of 206.8 kPa (30 psig) to 344.7 kPa (50 psig) and temperatures ranging from 230° C. to 260° C. Vapors produced during the method (e.g., water/steam and glycol) can be vented to a reflux column or distillation column and recovered and returned to the esterification vessel/reactor or zone (in the case of the glycol by-product) or discharged to waste (in the case of condensed water produced from steam condensation). A monomer is produced from this step, namely bis-(2-hydroxyethyl)-terephthalate (or "BHET"), which can be delivered to a second esterification and/or a polymerization reactor or zone wherein the BHET is polymerized to PET.

In some embodiments, the method can further comprise converting any o-xylenes of the xylene product mixture to phthalic anhydride. In some embodiments, converting the o-xylene to phthalic anhydride can comprise processing the o-xylene at oxidation conditions known to those of skill in the art with the benefit of the present disclosure. The o-xylene can be processed at oxidation conditions when present in an effluent comprising the xylene product mixture, or a stream comprising o-xylene can first be separated from the effluent comprising the xylene product mixture. In embodiments where a stream of the o-xylene is separated from the hydrogenation zone effluent comprising the xylene product mixture, the hydrogenation zone effluent is passed to a fractionation zone wherein the stream of o-xylenes is isolated from the hydrogenation zone effluent. The fractionation zone can comprise a separation column or other component suitable for fractionation through which the hydrogenation zone effluent comprising the xylene product mixture is passed. Fractionation techniques suitable for this step and/or other fractionation steps contemplated herein are described in more detail below. In some embodiments, the method can further comprise drying the effluent comprising the xylene product mixture. In some embodiments, the hydrogenation zone effluent can be dried prior to passing it to the fractionation zone. In some additional embodiments, the method can further comprise drying the stream of o-xylene. In some embodiments, the method can further comprise drying both the hydrogenation zone effluent comprising the xylene product mixture and the stream of o-xylene.

Fractionation is a commonly used method for many processes in many industrial plants to separate chemicals. In the present disclosure, a first fractionation zone may be used to separate saturated cyclic compounds, such as dimethylcyclohexane, and some lighter compounds from a C8 aromatics stream. Unlike other technologies, the disclosed method embodiments do not produce high volumes of C9 aromatics, so a fractionation column that is typically known as a "xylene column," which is a large and costly fractionation column to separate C9 aromatics from C8 aromatics, is not necessary. The fractionation column of the first fractionation zone is far smaller with fewer theoretical stages since C9 aromatics are not present in appreciable amounts and do not need to be separated from the C8 aromatics. The overall cost, including both the capital cost and the operating cost, of the first fractionation zone is dramatically reduced compared to systems where C9 aromatics need to be separated from C8 aromatics.

The C8 aromatics from the first fractionation zone are then passed to a second fractionation zone. It is often difficult to use conventional fractional distillation technology to separate different xylene isomers and ethylbenzene, if present, efficiently and economically because the boiling points of such C8 aromatics fall within a very narrow 8° C. range, from about 136° C. to about 144° C. (see Table 1). The boiling points of p-xylene and ethylbenzene are about 2° C. apart, and the boiling points of p-xylene and m-xylene are only about 1° C. apart. As a result, large equipment, significant energy consumption, and substantial recycles are typically required to provide effective and satisfactory xylene separations.

TABLE 1

| C8 Compound | Boiling Point (° C.) | Freezing Point (° C.) |
| --- | --- | --- |
| Ethylbenzene | 136 | −95 |
| p-xylene | 138 | +13 |
| m-xylene | 139 | −48 |
| o-xylene | 144 | −25 |

However, due to the unique hydrogenation zone effluent having a non-equilibrium mixture of xylenes, and specifically, having lower than equilibrium amounts of m-xylene, the fractionation in the second fractionation zone may be successfully accomplished by less costly equipment. It is not necessary for the equipment to separate the p-xylene and m-xylene because the amount of m-xylene in the hydrogenation zone effluent is not an equilibrium amount of m-xylene, and in many embodiments will be substantially less than an equilibrium amount of m-xylene. For example, it is accepted that an equilibrium reaction for the conversion of toluene to xylenes and benzene products normally provides m-xylene in an amount from 64 mol % at −23.2° C. to 51 mol % at 276.9° C., such as 62 mol % at −23.2° C. to 53 mol % at 276.9° C., or 60 mol % at −23.2° C. to 55 mol % at 276.9° C., or 58 mol % at −23.2° C. to 56 mol % at 276.9° C. In contrast, the hydrogenation zone effluent obtained with the presently disclosed method may comprise less than 50 wt % of the m-xylene equilibrium concentration, such as from greater than 0 wt % up to 49 wt % or greater than 0 wt % up to 45 wt %, or greater than 0 wt % to 40 wt %, or greater than 0 wt % to 35 wt %, greater than 0 wt % to 30 wt %, greater than 0 wt % to 20 wt %, greater than 0 wt % to 10 wt %, greater than 0 wt % to 5 wt %, or greater than 0 wt % to 1 wt % of the m-xylene equilibrium concentration.

Furthermore, it is not necessary to achieve a pure p-xylene stream from the second fractionation zone and one effluent of the second fractionation zone may contain a mixed xylene stream enriched in p-xylene, o-xylene, and trace m-xylene. With partial separation from the second fractionation zone being acceptable for the success of the disclosure, further cost savings are achieved. In one embodiment, the second fractionation zone is designed to achieve chemical grade o-xylene in the overhead, and once that is achieved, the remainder of all components may be removed in the bottoms. Thus, in some embodiments, a second effluent from the second fractionation zone can contain a stream enriched to 99 wt % o-xylene, which may be collected and passed for other uses as discussed herein.

In some embodiments, the mixed xylene steam from the second fractionation zone is passed to a crystallizer. Crystallizers can be used to purify the mixed xylene stream to polymer grade p-xylene. In some embodiments, the mixed xylene stream feed to the crystallizer may comprise less than 70 wt % p-xylene, which may benefit from one or more stages of crystallizers to produce polymer grade p-xylene at acceptable recoveries. In one embodiment, the mixed xylene stream resulting from fractionation will be 70 wt % or greater p-xylene, which can provide acceptable recoveries of polymer grade p-xylene using a single stage crystallizer. In some embodiments, 99.5 wt % or 99.8 wt % p-xylene can be obtained. In particular embodiments, at least 99.5 wt % or at least 99.8 wt % p-xylene is obtained.

Crystallizers take advantage of the differences between the freezing points and solubilities of the C8 aromatic components at different temperatures. With its higher freezing point, p-xylene is usually separated as a solid, while the other components are recovered in a p-xylene depleted filtrate. Crystallization results in polymer-grade purity p-xylene, which typically is needed for commercial conversion of p-xylene to terephthalic acid. Suitable crystallization processes are described in U.S. Pat. Nos. 4,120,911 and 3,662,013, the relevant portions of which are incorporated herein by reference, and components used in such methods are commercially available.

In some embodiments, a first and second fractionation zone that is reduced in size and utility cost, combined with one or more crystallizers, is a cost effective approach that can be used with the disclosed method to achieve polymer grade p-xylene that capitalizes on the unique advantages afforded by the composition of the hydrogenation zone effluent of the present disclosure.

In any or all of the described embodiments, the method can further comprise separating an unreacted reactant from an effluent produced during the method and recycling the unreacted reactant to the zone from which it was obtained and/or an upstream zone (wherein "upstream" is intended to indicate one or more previous zones relative to the zone from which the unreacted reactant is obtained). Solely by way of example, unreacted ethanol can be recycled from the oxidation zone by passing any unreacted ethanol back into the oxidation zone, either via an independent inlet of the reactor or container of the oxidation zone, or by recombining the unreacted ethanol with the feed stream and adding the mixture into a feed stream inlet of the reactor or container. Such recycling can be used to increase the yield of acetaldehyde produced by the oxidation zone. In yet other embodiments, any unreacted acetaldehyde from the dimerization zone can be recycled back to the dimerization zone so as to increase the amount of 2-butenal in the effluent produced from the dimerization zone. In such embodiments, the unreacted acetaldehyde can be recycled back into the dimerization zone either via an independent inlet of the reactor or container of that zone, or by recombining it with the effluent comprising acetaldehyde produced by the oxidation zone. In yet some additional embodiments, any unreacted 2-butenal from the cyclization zone can be recycled back to the cyclization zone to increase the amount of o-methylbenzaldehyde and p-methylbenzaldehyde produced by the cyclization zone. In such embodiments, the unreacted 2-butenal can be recycled back into the cyclization zone either via an independent inlet of the reactor or container of that zone, or by recombining it with the effluent comprising 2-butenal produced by the dimerization zone. In yet some additional embodiments, any unreacted o-methylbenzaldehyde and/or p-methylbenzaldehyde from the hydrogenation zone can be recycled back to the hydrogenation zone so as to increase the amount of the p-xylene and/or o-xylene in the xylene product mixture produced by the hydrogenation zone. In such embodiments, the unreacted o-methylbenzaldehyde and/or p-methylbenzaldehyde can be recycled back into the hydrogenation zone either via an independent inlet of the reactor or container of that zone, or by recombining it with the effluent comprising o-methylbenzaldehyde and p-methylbenzaldehyde produced by the cyclization zone. Any combination of these recycling embodiments can be used.

Figure 1B:
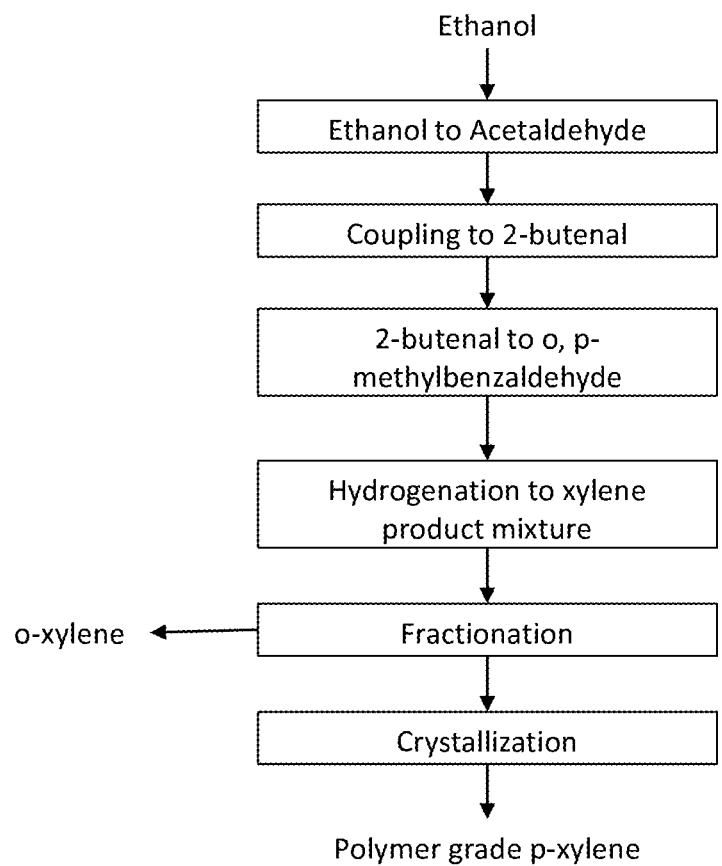

Steps and components of a representative method and system embodiment are summarized schematically in FIG. 1A. Representative method steps of further embodiments are summarized schematically in FIG. 1B. By way of example, FIG. 1A shows a flow scheme of one embodiment of the present disclosure. Syngas or industrial gas in line 104 and, optionally, hydrogen in line 102, are passed to gas fermentation zone 100 having at least one gas fermentation bioreactor comprising at least one C1-fixing bacteria in a liquid nutrient medium to generate gas fermentation zone effluent 106 comprising ethanol. Gas fermentation zone effluent 106 comprising ethanol is passed to oxidation zone 110 where it is contacted with an oxidation catalyst under oxidation conditions and produce oxidation zone effluent 108 comprising acetaldehyde, which in turn is passed to dimerization zone 120 where it is contacted with a dimerization catalyst under dimerization conditions and produce a dimerization zone effluent 112 comprising 2-butenal. Dimerization zone effluent 112 is passed to cyclization zone 130 where it is contacted with a cyclization catalyst under cyclization conditions and produce cyclization zone effluent 114 comprising o-methylbenzaldehyde and/or p-methylbenzaldehyde, which in turn is passed to hydrogenation zone 140 where it is contacted with a hydrogenation catalyst comprising a first group VIII metal (IUPAC 8, 9, and 10) optionally deposited on a support material under hydrogenation conditions to produce hydrogenation zone effluent 116 comprising a xylene product mixture, which comprises a non-equilibrium mixture of xylenes.

Hydrogenation zone effluent 116 is passed to first fractionation zone 150 where benzene-enriched stream is removed in overhead stream 118 and a dimethylcycohexane-enriched stream is removed in a bottoms stream 122. The remainder of hydrogenation zone effluent 116 is removed in stream 124 and passed to second fractionation zone 160. The amount of benzene may influence the point at which stream 124 is removed from the first fractionation zone, thus FIG. 1A shows a generic location, and does not indicate a sidecut per se. Chemical grade purity o-xylene stream 126 is removed from second fractionation zone as a bottoms stream, and xylene product stream 128 comprising p-xylene, o-xylene, and trace m-xylene is removed from second fractionation zone as an overhead stream.

Xylene product stream 128 is passed to crystallizer 170. Depending upon the composition of xylene product stream 128, crystallizer 170 may be controlled such that p-xylene product stream 134 has sufficiently high purity to meet polymer grade purity standards. The o-xylene filtrate stream 132 has a low enough content of p-xylene such that when o-xylene filtrate stream 132 is combined with stream 126 from the second fractionation zone, the combined stream still meets chemical grade purity levels for o-xylene. p-Xylene product stream 134 which is a stream of polymer grade purity p-xylene may be the final desired product stream of the process. Furthermore, as shown, p-xylene product stream may be derived from a source of recycled carbon as shown in FIG. 1A. Optionally, p-xylene product stream 134, or p-xylene product stream 138 discussed below, may be passed to a catalytic liquid phase oxidation reactor 190 for the conversation of the p-xylene to terephthalic acid, which is then removed in stream 144.

Shown in FIG. 1A is an optional second crystallizer 180. When xylene product stream 128 contains less than 70 wt % p-xylene, a second crystallizer 180 may be used. In this embodiment, the p-xylene product stream 134 from crystallizer 170 is passed to second crystallizer 180 to generate p-xylene product stream 138 having polymer grade p-xylene and o-xylene stream 136 having a sufficiently low amount of p-xylene so that after combining with stream 132 to form combined stream 137, and further combining with stream 126, the resulting combined stream 142 still meets chemical grade purity levels of o-xylene.

Another benefit of the flow scheme illustrated by FIG. 1A is that the crystallizers which are used are much smaller than those used in conventional production of polymer grade p-xylene. Small scale crystallizers may facilitate the ability to verify the purified polymer grade p-xylene obtained from recycled carbon or from a sustainable source. Some recycled carbon or sustainable sources of C1 substrates for gas fermentation to produce ethanol provide C1 substrates on a small scale and small scale crystallizers provide the ability to carry-out the process from the generation of ethanol by gas fermentation through purification of p-xylene on a scale commensurate with the C1 substrate supply for the gas fermentation which is useful to verify and certify the p-xylene is sustainable or derived from recycled carbon.

Products obtained from method embodiments disclosed herein can be used in various applications and techniques to make additional products such as articles of manufacture. In some embodiments, PET made according to a method embodiment of the present disclosure can be converted into various PET-based products or articles, such as containers (bottles, jars, cans, coolers, etc.), packaging materials (food containers, storage containers, etc.), fibers (e.g., threads and yarns for use in fabrics and textiles), and films (wrapping materials, liners, food wraps, etc.). In some embodiments, the PET material disclosed herein can be converted to such products using molding techniques suitable for PET processing. In some embodiments, the PET can be blow molded into a product using an extrusion or injection blow molding process. In extrusion blow molding, a parison of the PET material is placed in a mold and hot air is blown into the parison to inflate it into the form of the mold. The object is cooled, the mold opened, and the object ejected. In injection blow molding, the PET material is injection molded into a heated cavity, onto a core pin. The cavity mold forms the outer shape of the part and is based off a core rod which shapes the inside of a preform. The preform mold is opened and compressed air is injected into the preform and the object is blown, cooled, and then ejected. In some other embodiments, an object can be made from the PET material using a thermoforming technique, wherein a sheet of the PET material is heated to a temperature below its melting point to achieve a glassy or soft state and it is then stretched to contours of a mold. The material is then cut with a die to provide the desired formed object. In yet additional embodiments, melt spinning techniques can be used to make PET fibers, wherein the PET material (in the form of chips, granules, or the like) is melted to form a solution and then forced through holes of a spinneret, after which fibers of the material are drawn (stretched) to provide a fiber of a desired diameter.

IV. Overview of Several Embodiments

Disclosed herein are embodiments of a method, comprising: contacting a feed stream comprising ethanol with an oxidation catalyst under oxidation conditions to form an oxidation zone effluent stream comprising acetaldehyde; passing the oxidation zone effluent stream to a dimerization zone and contacting the oxidation zone effluent stream with a dimerization catalyst under dimerization conditions to produce a dimerization zone effluent stream comprising 2-butenal; passing the dimerization zone effluent stream to a cyclization zone and contacting the dimerization zone effluent stream with a cyclization catalyst under cyclization conditions to form a cyclization zone effluent stream comprising o-methylbenzaldehyde and/or p-methylbenzaldehyde; and passing the cyclization zone effluent stream to a hydrogenation zone and contacting the cyclization zone effluent stream with a hydrogenation catalyst comprising a first Group VIII metal deposited on a support material to produce a hydrogenation zone effluent comprising a non-equilibrium mixture of xylenes.

In any or all embodiments of the method, the hydrogenation catalyst further comprises a second Group VIII metal, a modifier component, or a combination thereof, all deposited on the support material wherein the second Group VIII metal is not the same as the first Group VIII metal.

In any or all of the above embodiments, the modifier component is selected from rhenium, tin, an alkali metal, an alkali earth metal, or any combination thereof.

In any or all of the above embodiments, the hydrogenation catalyst comprises the modifier component and wherein the support material is carbon, the first Group VIII metal is palladium, and the modifier component is rhenium.

In any or all of the above embodiments, the support material is selected from carbon material, a silica, an alumina, a silica-alumina, a titania, a zirconia, a zeolite, a zinc oxide, or any combination thereof.

In any or all of the above embodiments, the non-equilibrium mixture of xylenes comprises m-xylene in an amount ranging from 0 wt % to less than 40 wt % of a m-xylene equilibrium concentration.

In any or all of the above embodiments, the non-equilibrium mixture of xylenes comprises m-xylene in an amount ranging from 0 wt % to 20 wt % of a m-xylene equilibrium concentration.

In any or all of the above embodiments, the non-equilibrium mixture of xylenes comprises m-xylene in an amount ranging from 0 wt % to 5 wt % of a m-xylene equilibrium concentration.

In any or all of the above embodiments, the non-equilibrium mixture of xylenes comprises m-xylene in an amount ranging from 0 wt % to 1 wt % of a m-xylene equilibrium concentration.

In any or all of the above embodiments, the ethanol is (i) ethanol from liquid phase fermentation of cellulosic material and or sugar; (ii) ethanol from gas phase fermentation of industrial process waste or non-waste gas, internal combustion engine exhaust fumes, syngas, direct air capture, electrolysis, $CO_2$-containing gas or any combination thereof; (iii) ethanol from a source other than cellulosic material, sugar, industrial process waste or non-waste gas, internal combustion engine exhaust fumes, gasification processes, syngas, direct air capture, electrolysis, or $CO_2$-containing gas; or (iv) ethanol from hydration of ethylene; or any combination of (i), (ii), (iii), and/or (iv).

In any or all of the above embodiments, the industrial process is selected from ferrous metal products manufacturing, steel mill manufacturing, non-ferrous products manufacturing, petroleum refining, electric power production, carbon black production, paper and pulp production, ammonia production, methanol production, coke manufacturing, petrochemical production, carbohydrate fermentation, cellulosic fermentation, cement making, aerobic digestion, anerobic digestion, catalytic processes, natural gas extraction, oil extraction or any combination thereof; and/or wherein the syngas is from coal gasification, refinery residues gasification, petroleum coke gasification, biomass gasification, lignocellulosic material gasification, waste wood gasification, black liquor gasification, natural gas reforming, municipal solid or liquid waste gasification, refuse derived fuel gasification, sewerage or sewerage sludge gasification, sludge from waste water treatment gasification and/or industrial solid waste gasification or any combination thereof.

In any or all of the above embodiments, the conversion of acetaldehyde in the dimerization zone provides 15 wt % to 65 wt % of a product reaction mixture comprising 2-butenal; the selectivity of acetaldehyde to 2-butenal in the dimerization zone ranges from 57 wt % to 91 wt %; the conversion of 2-butenal in the cyclization zone provides 70 wt % to 95 wt % of a product reaction mixture comprising o-methylbenzaldehyde and p-methylbenzaldehyde; the selectivity of 2-butenal to o-methylbenzaldehyde and p-methylbenzaldehyde in the cyclization zone ranges from 50 wt % to 95 wt %; or any combination of any of the aforementioned.

In any or all of the above embodiments, the method further comprises passing the hydrogenation zone effluent to a fractionation zone and separating a stream comprising o-xylene from (i) a stream comprising p-xylene or (ii) a stream comprising p-xylene and m-xylene.

In any or all of the above embodiments, (i) the stream comprising p-xylene or (ii) the stream comprising p-xylene and m-xylene comprises a minimum amount of p-xylene, wherein the minimum amount of p-xylene ranges from a minimum of at least 65 wt % to a minimum of at least 85 wt %.

In any or all of the above embodiments, the method further comprises (i) drying the stream comprising the o-xylene; (ii) reacting the o-xylene in the stream comprising o-xylene under reaction conditions to form phthalic anhydride; or both (i) and (ii).

In any or all of the above embodiments, the method further comprises drying the hydrogenation zone effluent prior to passing it to the fractionation zone, and/or drying the stream comprising the o-xylene.

In any or all of the above embodiments, the method further comprises passing (i) the stream comprising p-xylene or (ii) the stream comprising p-xylene and m-xylene to a crystallizer and recovering a purified p-xylene stream comprising at least 99.5 wt % p-xylene.

In any or all of the above embodiments, the purified p-xylene stream comprises at least 99.8 wt % p-xylene.

In any or all of the above embodiments, the method further comprises reacting at least a portion of the p-xylene from the purified p-xylene stream under reaction conditions to form terephthalic acid.

In any or all of the above embodiments, the method further comprises reacting at least a portion of the terephthalic acid with ethylene glycol under reaction conditions to form polyethylene terephthalate.

In any or all of the above embodiments, the method further comprises forming the polyethylene terephthalate into one or more products.

In any or all of the above embodiments, the method further comprises one or more separation and/or recycling steps, wherein the recycling steps are selected from (i) recycling at least a portion of the oxidation zone effluent stream to the oxidation zone until a predetermined target concentration of acetaldehyde in the oxidation zone effluent stream is achieved; (ii) recycling at least a portion of the dimerization zone effluent stream to the dimerization zone until a predetermined target concentration of 2-butenal in the dimerization zone effluent stream is achieved; (iii) recycling at least a portion of the cyclization zone effluent stream to the cyclization zone until a predetermined target concentration of o-methylbenzaldehyde and/or p-methylbenzaldehyde in the cyclization zone effluent stream is achieved; (iv) recycling at least a portion of the hydrogenation zone effluent stream to the hydrogenation zone until a predetermined target concentration of xylenes in the hydrogenation zone effluent stream is achieved; and/or (v) any combination of steps (i), (ii), (iii), and/or (iv).

In any or all of the above embodiments, the method further comprises regenerating the cyclization catalyst by heating the cyclization catalyst under air.

Also disclosed herein are embodiments of an apparatus, comprising: a gas fermentation bioreactor in fluid communication with an oxidation reactor; the oxidation reactor in fluid communication with a dimerization reactor; the dimerization reactor in fluid communication with a cyclization reactor; the cyclization reactor in fluid communication with a hydrogenation reactor; the hydrogenation reactor in fluid communication with a first fractionation zone; the first fractionation zone in fluid communication with a second fractionation zone; and the second fractionation zone in fluid communication with a first crystallizer.

In any or all of the above embodiments, the apparatus further comprises a second crystallizer in fluid communication with the first crystallizer.

In any or all of the above embodiments, the apparatus further comprises a catalytic liquid phase oxidation reactor in fluid communication with the first crystallizer.

In any or all of the above embodiments, the apparatus further comprises a catalytic liquid phase oxidation reactor in fluid communication with the second crystallizer.

V. Examples

General Procedure for Batch High Throughput Method used in Examples 9-15: Powdered catalysts were weighed out into 2 mL glass reaction vials, performed in triplicate. 48 vials were assembled onto one high throughput plate, which was then sealed and reduced under 5% $H_2/N_2$ reduction gas, ramping at 2° C./minute to 300° C. and holding for 4 hours.

The sealed reactor was transferred to a flow-through $N_2$ purge box, where it was unsealed and each vial was filled with 1.75 mL of reactant solution with a composition of 12.5 wt % o-methylbenzaldehyde, 12.5 wt % p-methylbenzaldehyde and remainder dodecane solvent. The reactor was resealed and transferred out of the purge box and connected to an automated batch reactor setup. Run operation began with 3 cycles of reactor pressurization to 100 psi $H_2$ to purge out air in the lines, before flowing pure $H_2$ until the desired pressure is reached. All lines were sealed so that the reactor was isolated, with 48 individual vials sharing the headspace. The reactor was heated at 4° C./minute while being shaken in a circular motion at 600 RPM to facilitate mass transfer. After reaching target temperature and then holding for the length of the experiment, the reactor was cooled down to room temperature before the pressure was released. GC-FID analysis was used to quantitate the products.

Example 1

Figure 2:
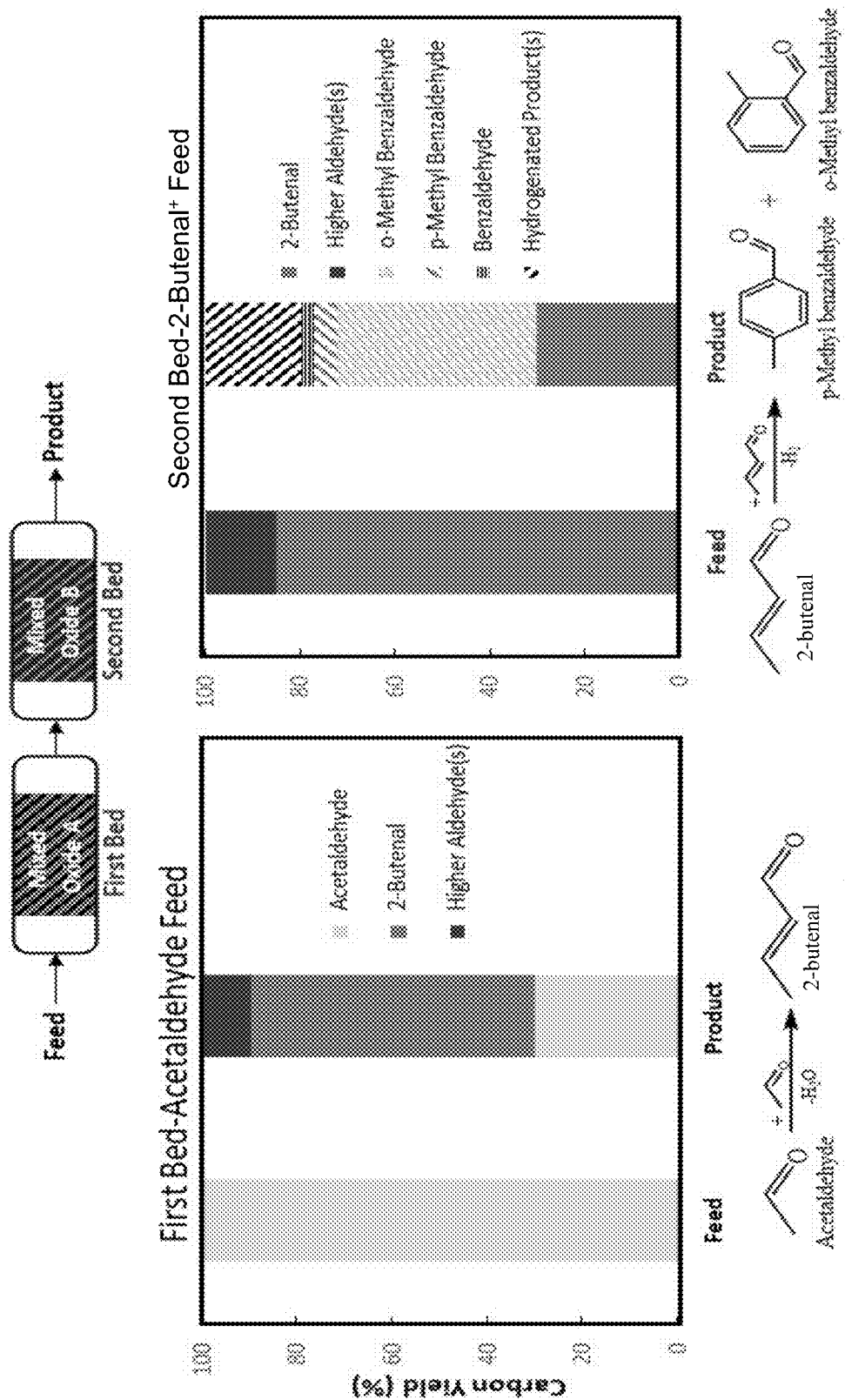
FIG. 2 shows results obtained from evaluating carbon yield (%) for a representative method for making ortho-methylbenzaldehyde (or "o-methylbenzaldehyde") and para-methylbenzaldehyde (or "p-methylbenzaldehyde") products from acetaldehyde using (i) a dimerization step in a dimerization zone to produce 2-butenal from acetaldehyde and (ii) a cyclization step using a cyclization zone to produce the ortho-methylbenzaldehyde and para-methylbenzaldehyde products from the 2-butenal made in the dimerization zone.

In this example, a representative dimerization reaction that takes place in a dimerization zone as described herein was evaluated. The feed composition used in this particular example was ethanol-derived acetaldehyde. Results of particular examples are shown in FIG. 2. And, data from particular examples are provided in Table 2.

TABLE 2

| Catalyst Composition | Conditions | | | Conversion (%) | Aldehyde Selectivity (%) | |
|---|---|---|---|---|---|---|
| | T (° C.) | P (psig) | P (kPa) | | 2-butenal | C4+ Total* |
| MnO—ZnO—ZrO$_2$ | 180 | 150 | 1034 | 64.8% | 90.8% | 96.9% |
| | 300 | 110 | 758 | 58.9% | 83.9% | 95.4% |
| MgO—Al$_2$O$_3$ | 180 | 100 | 689.5 | 20.0% | 81.1% | 96.8% |
| | 300 | 110 | 758 | 60.8% | 57.9% | 82.9% |
| ZnO—ZrO$_2$ (10:1) | 180 | 110 | 758 | 24.1% | 87.5% | 92.0% |
| ZnO—ZrO$_2$ (2:1) | 180 | 110 | 758 | 32.0% | 90.0% | 95.9% |
| TiO$_2$ | 180 | 110 | 758 | 15.1% | 77.4% | 94.8% |

*C4+ Total: Sum of 2-butenal (C4), hexadienal (C6), octatrienal (C8)

Example 2

Figure 3:
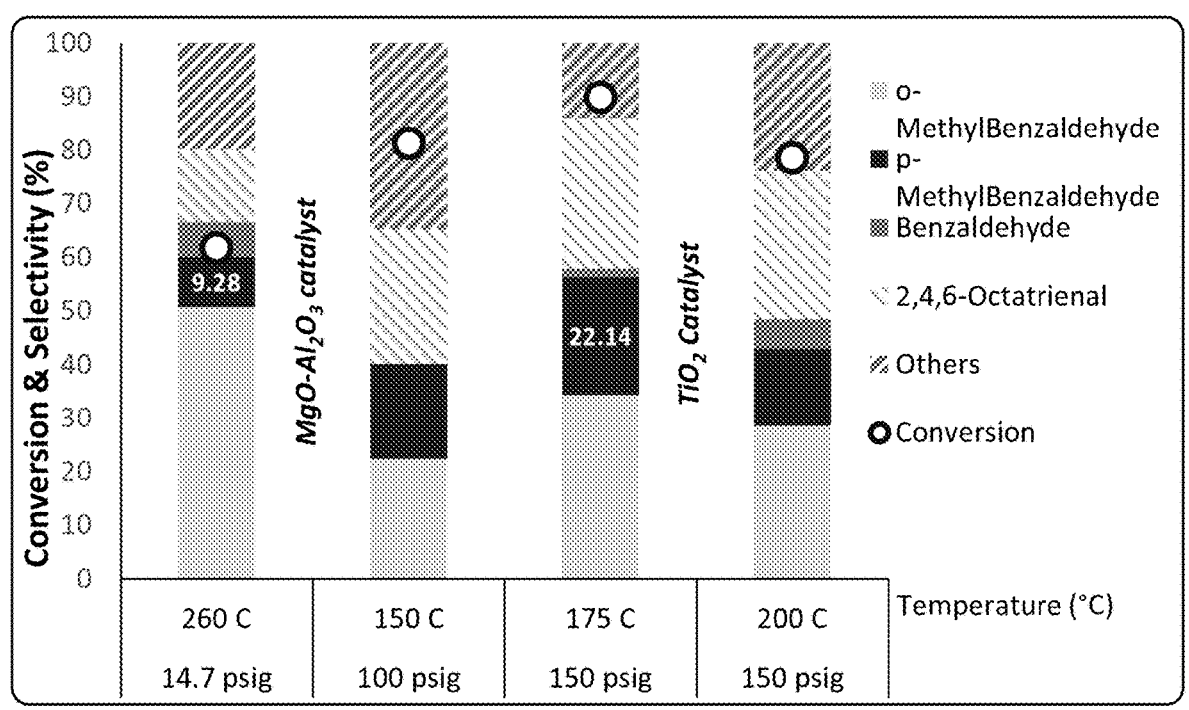
FIG. 3 shows results obtained from evaluating conversion and selectivity (%) for a cyclization step, wherein 2-butenal is reacted with a catalyst at varying temperature and pressure; bar A summarizes reaction product distribution for a cyclization step using a temperature of 260° C. and a pressure of 101.35 kPa (14.7 psig); bar B summarizes reaction product distribution for a cyclization step using a temperature of 150° C. and a pressure of 689.5 kPa (100 psig); bar C summarizes reaction product distribution for a cyclization step using a temperature of 175° C. and a pressure of 1034 kPa (150 psig); and bar D summarizes reaction product distribution for a cyclization step using a temperature of 200° C. and a pressure of 1034 kPa (150 psig).
Figure 4:
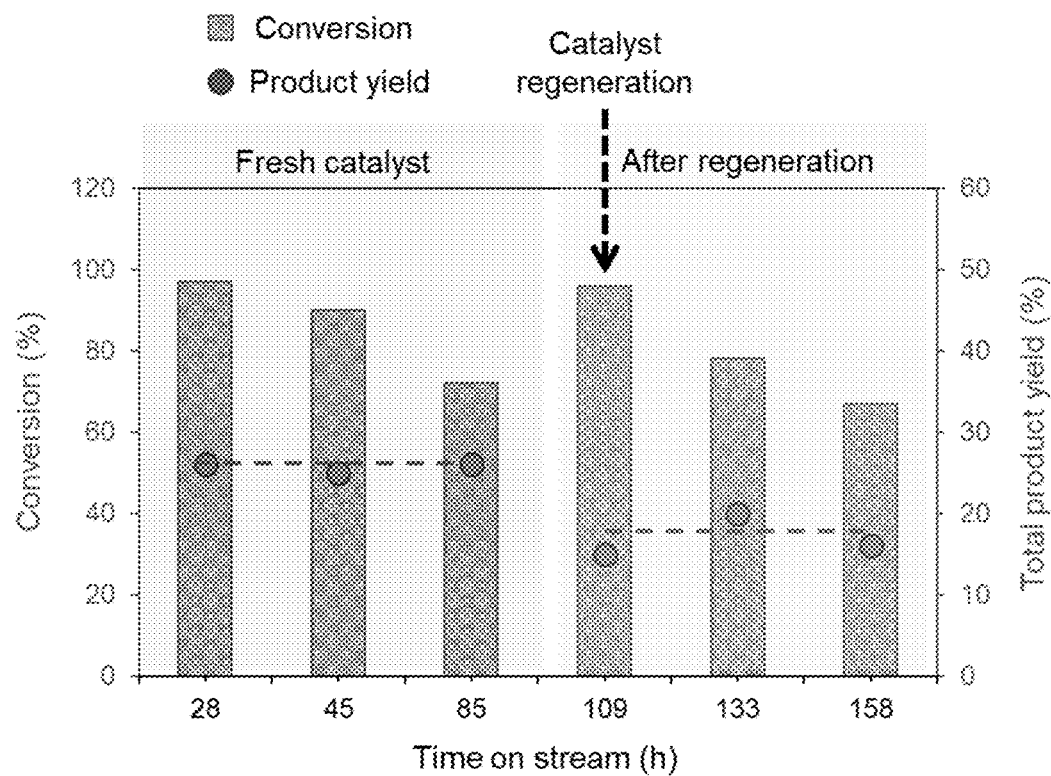
FIG. 4 shows conversion and total product yield results for condensing and cyclizing 2-butenal using fresh and regenerated $TiO_2$ catalyst.

In this example, a representative cyclization reaction that takes place in a cyclization zone as described herein was evaluated. The feed composition used in this particular example was 2-butenal. Results from a particular example are shown in FIG. 3. FIG. 4 also shows results from an example wherein both the 2-butenal conversion and the corresponding total product yield obtained during condensation reaction at 300° C. using a TiO$_2$ catalyst were obtained. In this example, the TiO$_2$ catalyst surface area was 60 m$^2$/g, the reaction temperature was 300° C. (conducted at atmospheric pressure), and the WHSV was 0.2 h$^{-1}$. Very high 2-butenal conversion (~95%) was achieved with a fresh TiO$_2$ catalyst. In some examples, decreased conversion, along with the time on stream, suggested catalyst deactivation. While the conversion was decreased from ~95% to ~70% for some examples, the yield of the total product remained constant (~25%). The products that were detected by GC-MS in some examples included 2,4,6 octatrienal, o-methylbenzaldehyde and p-methylbenzaldehyde, o-xylene and benzaldehyde. Without being limited to a single theory, it is believed that the low carbon balance obtained in some examples is attributed to the formation of long chain oligomeric products that are not detectable in the GC-MS. Effective regeneration of the TiO$_2$ catalyst was also demonstrated—see FIG. 4. The 2-butenal conversion was very similar as was obtained in the fresh catalyst. However, the yield of the products was ~15%, which currently is believed to suggest that although a regenerated catalyst provides similar 2-butenal conversion, it also favors the formation of long chain oligomeric products. In some examples, the TiO$_2$ catalyst obtained after regeneration was further deactivated after time on stream, however, the total yield of the products did not change significantly.

Figure 5:
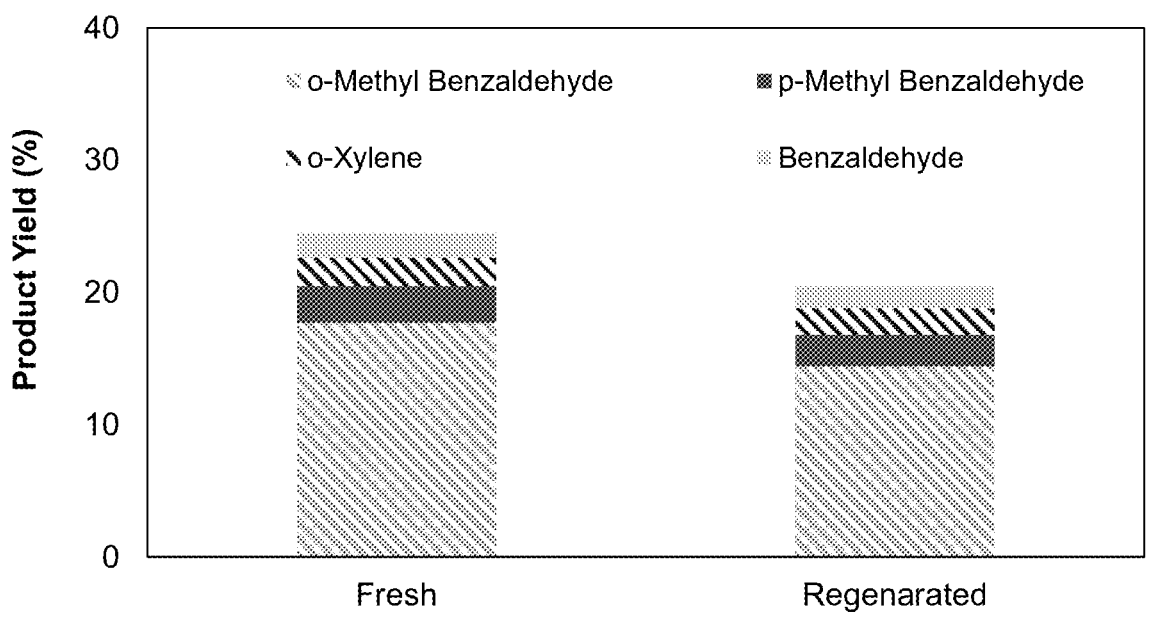
FIG. 5 shows the product distribution obtained from condensing and cyclizing 2-butenal using fresh and regenerated $TiO_2$ catalyst.

Product distribution yield results obtained during an example of the 2-butenal condensation/cyclization step is shown in FIG. 5. Condensation and cyclization of C4, 2-butenal, yielded cyclic C8 products, such as p-methylbenzaldehyde and o-methylbenzaldehyde, and an acyclic C8 product, such as 2,4,6 octatrienal. Among these products, o-methylbenzaldehyde was obtained as the major product. A very similar trend in product distribution was obtained with both fresh and regenerated catalysts, although the overall yield was higher in the case of fresh catalyst. Without being limited to a single theory, it currently is believed that the formation of o-xylene might be attributed to o-methylbenzaldehyde reduction to the corresponding benzyl alcohol, followed by hydrodeoxygenation. The Bronsted acidity present in the TiO$_2$ catalyst may catalyze the hydrodeoxygenation reaction at higher temperature.

Example 3

Figure 6A:
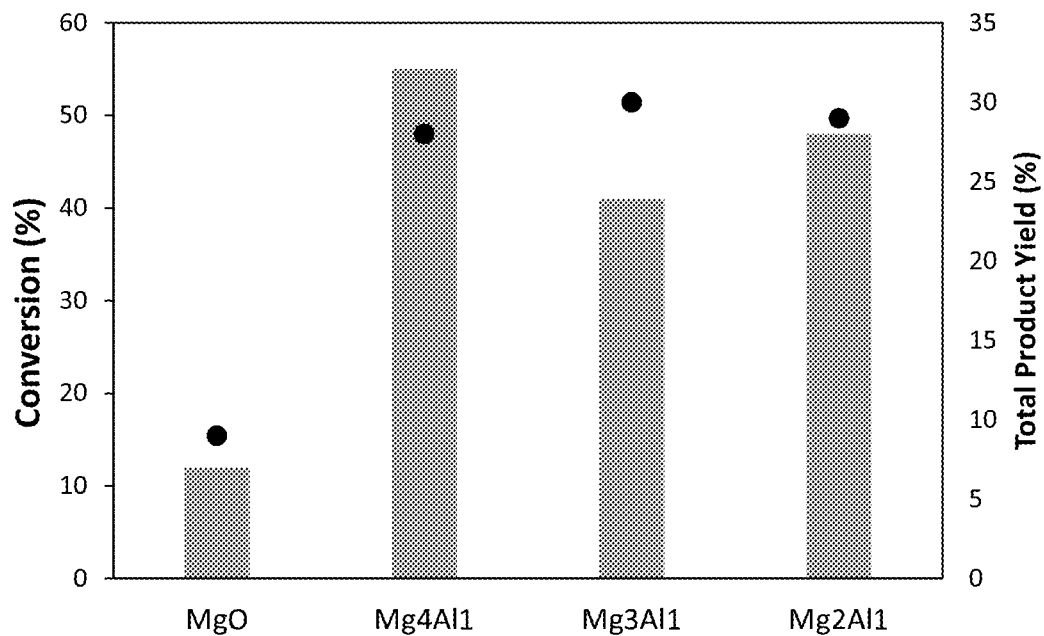
FIGS. 6A and 6B show conversion and total product yield results for condensing and cyclizing 2-butenal to methylbenzaldehyde (FIG. 6A), and the corresponding product distribution obtained using different hydrotalcite-based catalysts (FIG. 6B).
Figure 6B:
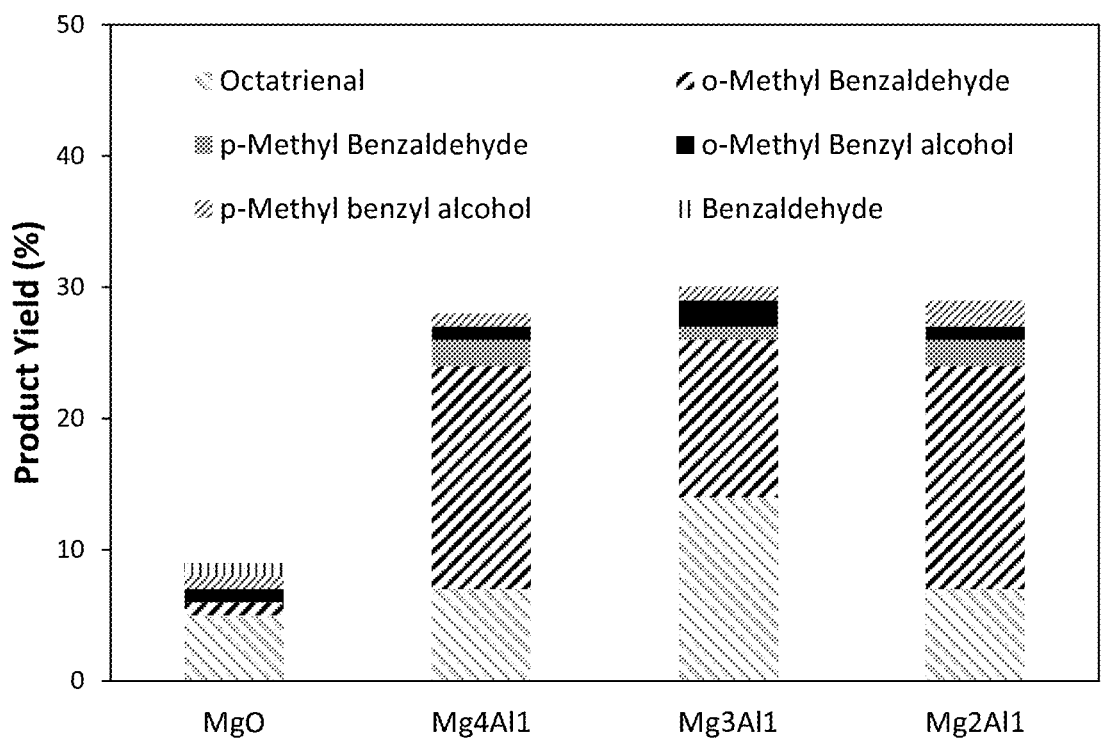

In this example, different hydrotalcite-based catalysts were evaluated for the condensation of 2-butenal. The results obtained from theses catalysts at different process condition are shown in FIGS. 6A and 6B. In these examples, the reaction conditions were a temperature of 300° C., atmospheric pressure, and a WHSV of 0.23 h$^{-1}$. All the hydrotalcite catalysts (MgO/Al$_2$O$_3$) showed higher activity compared to the MgO catalyst as evidenced by the higher conversion of 2-butenal as shown in FIG. 6A. Only ~10% conversion was achieved with the MgO catalyst; however, hydrotalcite-based catalysts showed ~50% conversion. The total product yield obtained in theses catalyst was ~35%, further suggesting good carbon balance using these catalysts. Thus, although hydrotalcite catalysts provide lower conversion compared to TiO$_2$ catalysts, it is believed that they can prevent formation of unwanted long chain oligomeric products. FIG. 6A also shows the correlation between the effect of Al content in the hydrotalcite catalyst and the corresponding activity for 2-butenal condensation. Although the Mg$_4$Al$_1$ catalyst showed a 3-fold increase in conversion compared to the MgO catalyst, further increase in Al content (i.e., Mg$_4$Al$_1$→Mg$_3$Al$_1$→Mg$_2$Al$_1$) did not show much impact as both conversion and product yield were similar in the examples with higher Al content. FIG. 6B shows the corresponding product distribution obtained with different catalysts. The products in FIG. 6B included 2,4,6 octatrienal, 2-methylbenzaldehyde (or o-methylbenzaldehyde), 2-methyl benzyl alcohol, 4-methyl benzaldehyde (or p-methylbenzaldehyde), 4-methyl benzyl alcohol, and benzaldehyde.

Example 4

Figure 7:
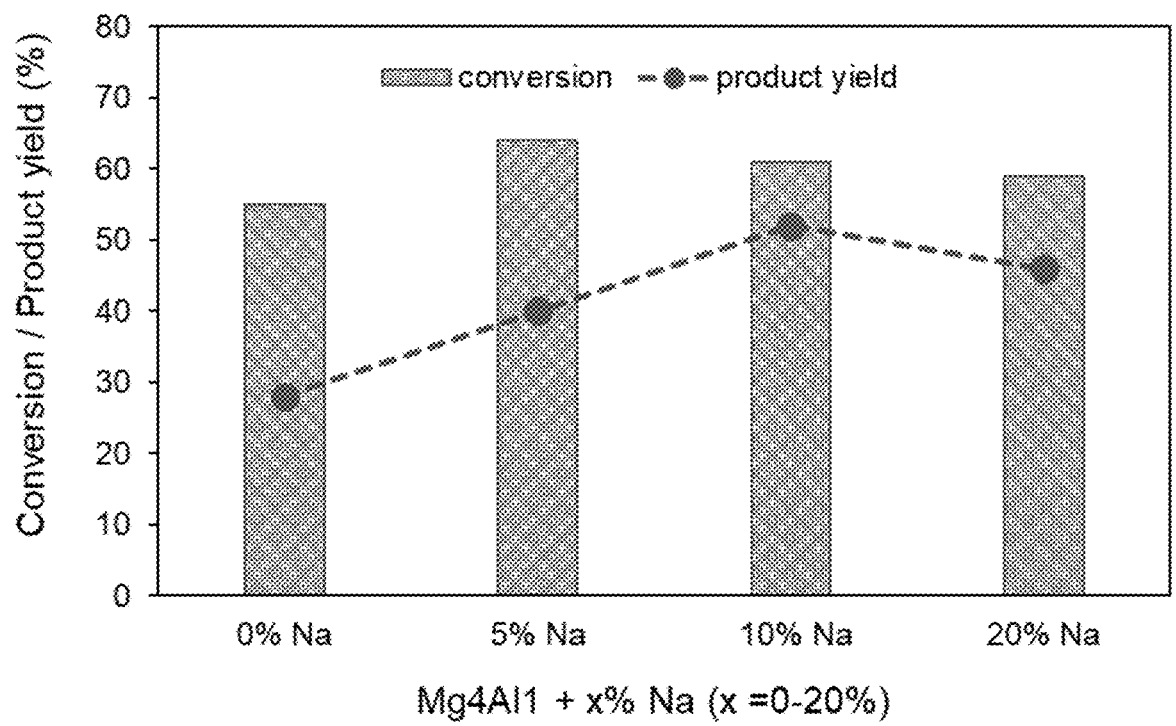
FIG. 7 shows conversion and total product yield results for condensing and cyclizing 2-butenal to methylbenzaldehyde using an $Mg_4Al_1$ catalyst with varying amounts of Na.

In this example, hydrotalcite-based catalysts comprising different amounts of impregnated Na were evaluated for the condensation of 2-butenal. $Mg_4Al_1$-x % Na (x=0-20%) was prepared by impregnating $Mg_4Al_1$ catalyst with different amount of Na. FIG. 7 shows the conversion and yield of the products obtained with $Mg_4Al_1$ catalyst containing varying Na amounts. In this example, the reaction conditions were a temperature of 300° C. at atmospheric pressure and a WHSV of 0.23 h$^{-1}$. While the incorporation of different amounts of Na did not have significant impact on conversion of 2-butenal, the overall product yield was increased with increasing Na content, up to 10 wt %.

Example 5

Figure 8:
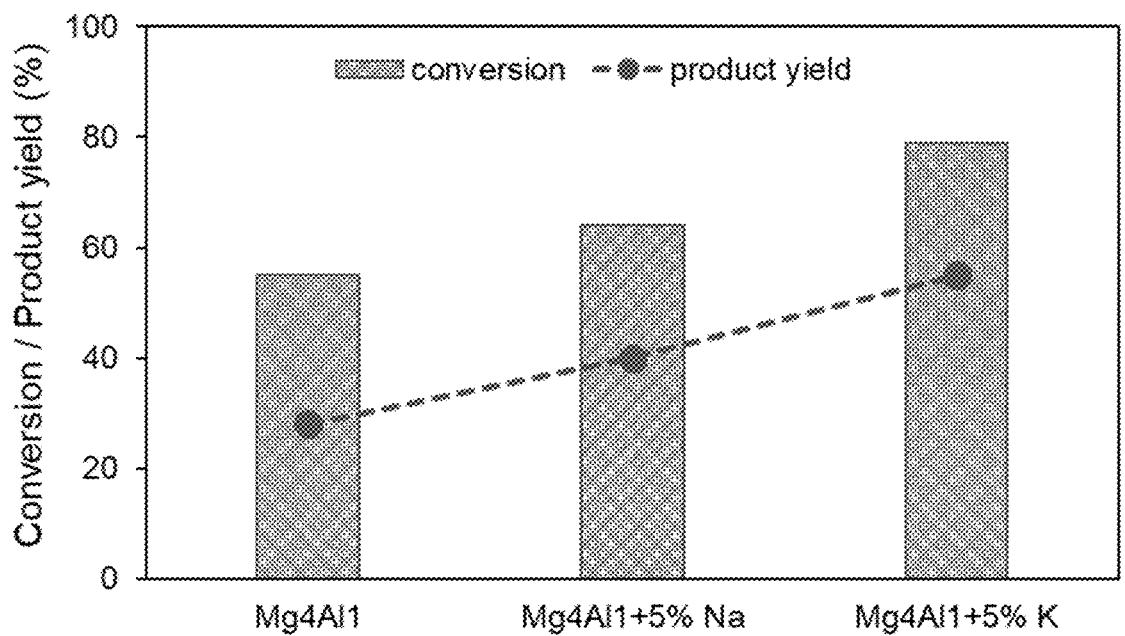
FIG. 8 shows conversion and total product yield results for condensing and cyclizing 2-butenal to methylbenzaldehyde using a $Mg_4Al_1$ catalyst with Na or K.

In this example, condensation of 2-butenal was investigated using a $Mg_4Al_1$ catalyst containing different alkali metals at a 5 wt. % loading. FIG. 8 shows the conversion and yield of the products obtained with the $Mg_4Al_1$+5 wt. % M (where M is Na or K) catalysts versus a catalyst containing only $Mg_4Al_1$. The reaction conditions were a temperature of 300° C. at atmospheric pressure and a WHSV of 0.22 h$^{-1}$. The catalysts containing an alkali metal showed both increased conversion and product yield compared to pure $Mg_4Al_1$ catalyst with K being more active than Na.

Example 6

Figure 9:
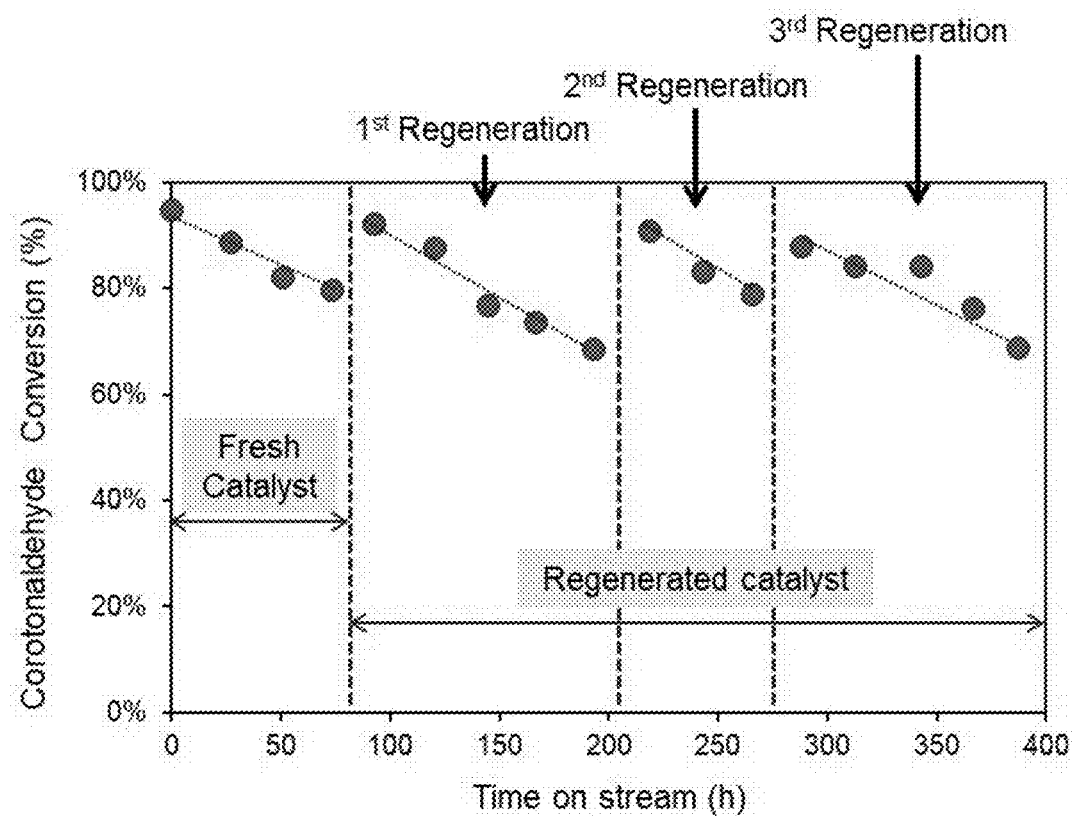
FIG. 9 shows conversion results obtained from evaluating the effect of $Mg_4Al_1$ catalyst regeneration on converting of 2-butenal to methylbenzaldehyde.
Figure 10:
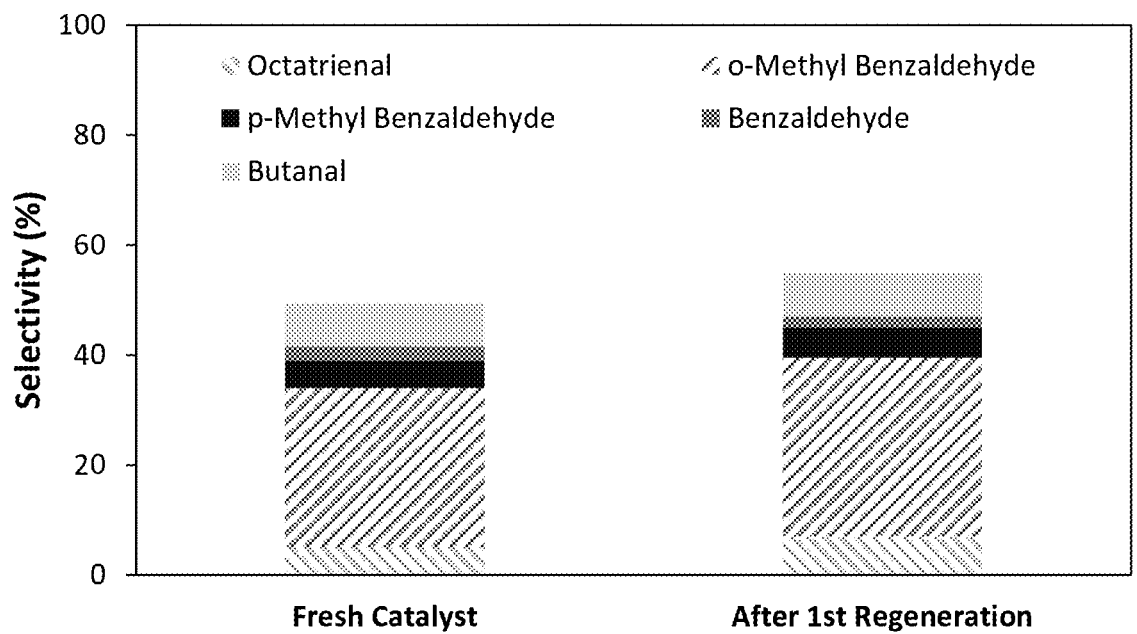
FIG. 10 shows product selectivity results obtained from evaluating the effect of $Mg_4Al_1$ catalyst regeneration on converting of 2-butenal to methylbenzaldehyde.

In this example, the effects of $Mg_4Al_1$ catalyst regeneration on performance was evaluated. FIG. 9 shows regeneration of $Mg_4Al_1$ catalyst and consequent effect on catalytic performance. The reaction conditions were a temperature of 300° C. at atmospheric pressure and a WHSV of 0.22 h$^{-1}$. After the catalyst activity had decreased to 80% conversion of 2-butenal, it was regenerated at 550° C. for 2 hours under air. As shown in FIG. 9, the catalytic activity was regained after a first regeneration, as both 2-butenal conversion product yield were very similar to those of the fresh catalyst. The first regenerated catalyst was again tested for condensation of 2-butenal until conversion had dropped to about 70%. The catalyst was again regenerated under the above conditions and its conversion and products yield were again restored to about the same performance as the fresh catalyst. The second regenerated catalyst was again tested for condensation of 2-butenal until conversion had dropped to about 80%. The catalyst was regenerated a third time under the above conditions and its conversion and product yield was again restored to about the same performance as the fresh catalyst. Using three regenerations, the catalyst life was extended to over 400 hours. FIG. 10 shows the product selectivity was improved slightly with the regenerated catalyst.

Example 7

Figure 11:
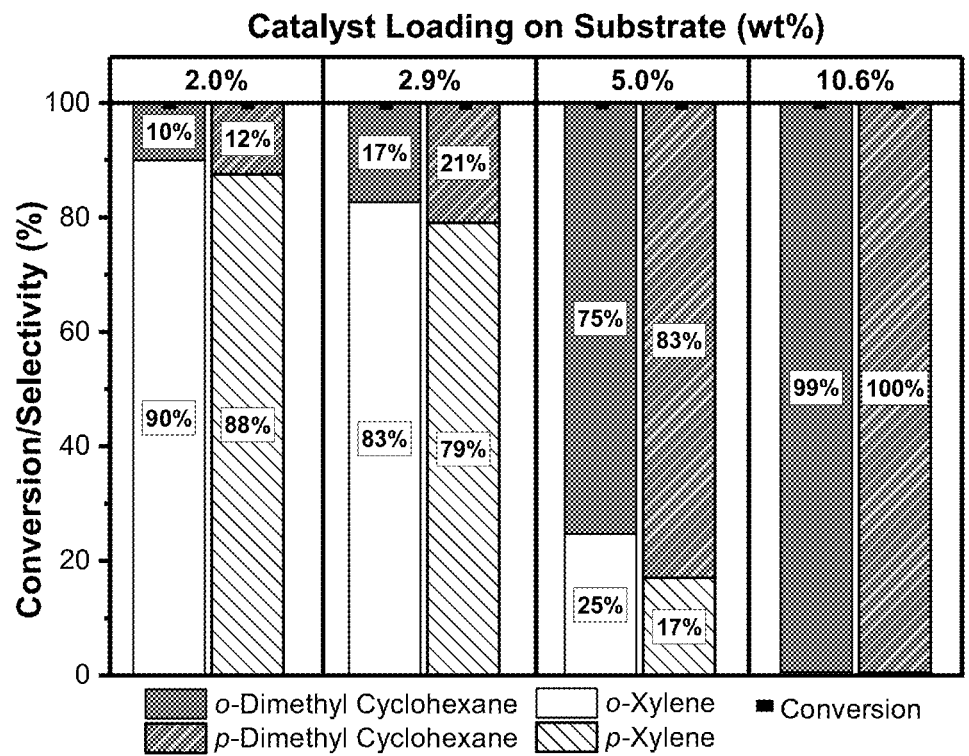
FIG. 11 shows conversion and selectivity (%) results obtained for a hydrogenation step, wherein a mixture comprising ortho/para methylbenzaldehyde was reacted with a Pd catalyst and a Re modifier component at 180° C. and 6895 kPa (1000 psig) $H_2$ for six hours using different amounts of the Pd/Re catalyst system (i.e., 2 wt %, 2.9 wt %, 5 wt %, and 10.6 wt %); "DMC" is dimethyl cyclohexane.

In this example, a cyclization reaction that takes place in a hydrogenation zone as described herein was evaluated. A batch reaction was conducted using reaction conditions of: 180° C., 6894.7 kPa (1000 psig) $H_2$, and a reaction time of 6 hours. Different catalyst loadings on a carbon support material were used, namely 2 wt %, 2.9 wt %, 5 wt %, and 10.6 wt % (expressed as the amount of metal per total weight of catalyst) of a 3 wt % Pd/6 wt % Re catalyst mixture. Results are shown in FIG. 11.

Example 8

In this example, different catalysts were evaluated for use in a hydrogenation reaction that takes place in a hydrogenation zone as described herein. The feed composition used in this particular example was a mixture of 50% p-methylbenzaldehyde and 50% o-methylbenzaldehyde in dodecane. The feed to solvent ratio was 1 to 4. The reaction temperature was 150° C. and the reaction pressure was 3447.4 kPa (500 psig). The reaction was run for a time period of 30 minutes. Conversion rates and carbon yield obtained using eight different hydrogenation catalyst compositions are presented in Table 3.

TABLE 3

| SI # | Catalyst Composition | Conversion, % Methylbenzaldehyde | | Carbon Yield, % | | | |
|---|---|---|---|---|---|---|---|
| | | | | Methylbenzyl Alcohol | | Xylene | |
| | | Para | Ortho | Para | Ortho | Para | Ortho |
| 1 | 3 wt % Pd/6 wt % Re on Carbon | 100.0 | 100.0 | 0.0 | 0.0 | 50.0 | 50.0 |
| 2 | 1.5 wt % Pd/3 wt % Re on Carbon | 100.0 | 100.0 | 0.0 | 0.0 | 50.0 | 50.0 |
| 3 | 0.75 wt % Pd/5 wt % Re on Carbon | 100.0 | 100.0 | 0.0 | 0.0 | 49.5 | 50.0 |
| 4 | 3 wt % Pd/6 wt % Re on $Al_2O_3$ | 100.0 | 100.0 | 0.0 | 0.0 | 48.3 | 50.0 |
| 5 | 1.5 wt % Pd/3 wt % Re on $Al_2O_3$ | 100.0 | 100.0 | 0.0 | 0.0 | 38.8 | 42.4 |
| 6 | 0.75 wt % Pd/5 wt % Re on $Al_2O_3$ | 100.0 | 100.0 | 32.1 | 28.0 | 19.2 | 22.4 |
| 7 | 1.5 wt % Pd on $Al_2O_3$ | 100.0 | 100.0 | 24.1 | 20.8 | 24.0 | 26.2 |
| 8 | 1.5 wt % Pd on $ZrO_2$ | 94.9 | 95.5 | 25.3 | 20.1 | 18.9 | 21.8 |

Example 9

In this example, combinatorial batch processes were evaluated using 3 wt % Pd 6 wt % Re/Hyperion C with the catalyst present at 2 wt % of the feed. Temperature, pressure, and reaction time were evaluated, with results presented in Table 4.

TABLE 4

| Temp. | Pressure (psig) | Pressure (kPa) | Reaction Time (hours) | Conversion | | Xylene Selectivity | | Dimethyl Cyclohexane Selectivity (%) | | Methyl Benzyl Alcohol Selectivity | |
|---|---|---|---|---|---|---|---|---|---|---|---|
| | | | | p | o | p | o | p | o | p | o |
| 180° C. | 1000 | 6894.7 | 6 | 100 | 100 | 90.9 | 87.6 | 10.1 | 12.4 | 0 | 0 |
| 150° C. | 1000 | 6894.7 | 1 | 100 | 100 | 100 | 100 | 0 | 0 | 0 | 0 |
| 150° C. | 500 | 3447.4 | 0.5 | 100 | 100 | 100 | 100 | 0 | 0 | 0 | 0 |
| 125° C. | 100 | 689.5 | 0.5 | 100 | 100 | 100 | 100 | 0 | 0 | 0 | 0 |

Example 10

In this example, combinatorial batch processes were evaluated using 3 wt % Pd 6 wt % Re on various carbon support materials. The reactions were run using reaction conditions comprising 125° C., 689.5 kPa (100 psig) $H_2$, a reaction time of 0.5 hours, and a catalyst concentration of 2 wt % of the total feed. Results for the different carbon support materials under these conditions are presented in Table 5.

TABLE 5

| | Conversion | | Xylene Selectivity | | Methyl Benzyl Alcohol Selectivity | |
|---|---|---|---|---|---|---|
| | p | o | p | o | p | o |
| Hyperion 07C | 100.0% | 100.0% | 100.0% | 100.0% | — | — |
| Hyperion 02C | 100.0% | 100.0% | 91.3% | 98.9% | 8.7% | 1.1% |
| NoritROX HF | 73.2% | 71.7% | 12.3% | 10.4% | 87.7% | 89.6% |
| Norit Darco-LS | 82.2% | 81.2% | 10.0% | 8.5% | 90.0% | 91.5% |
| Ceca | 73.2% | 71.7% | 12.3% | 10.4% | 87.7% | 89.6% |
| Pica | 89.1% | 87.1% | 12.0% | 11.7% | 88.0% | 88.3% |
| Jacobi | 77.6% | 75.2% | 2.6% | 2.1% | 97.4% | 97.9% |
| Nuchar | 90.8% | 88.0% | 7.3% | 7.7% | 92.7% | 92.3% |

Example 11

In this example, combinatorial batch processes were evaluated using different Group VIII metals (Pd, Pt, and Ru) on different metal oxide support materials ($Al_2O_3$, $ZrO_2$, and $TiO_2$). The reactions were run using reaction conditions of 150° C., 4136.8 kPa (600 psig) $H_2$, a reaction time of 0.5 hours, and a catalyst concentration of 2 wt % of the total feed. Results for the different Group VIII metals and support materials under these conditions are presented in Table 6.

TABLE 6

| Metal | Support | Conversion | | Xylene Selectivity | | Methyl Benzyl Alcohol Selectivity | |
|---|---|---|---|---|---|---|---|
| | | p | o | p | o | p | o |
| 1.5% Pd | $Al_2O_3$ | | | | | | |
| | $ZrO_2$ | 100.0% | 100.0% | 57.1% | 62.8% | 42.9% | 37.2% |
| | $TiO_2$ | 100.0% | 100.0% | 74.4% | 83.2% | 25.6% | 16.8% |
| 1.5% Pt | $Al_2O_3$ | 32.0% | 37.0% | 28.8% | 34.4% | 71.2% | 65.6% |
| | $ZrO_2$ | 11.3% | 14.1% | — | — | 100% | 100% |
| | $TiO_2$ | 6.1% | 7.4% | — | — | 100% | 100% |
| 1.5% Ru | $Al_2O_3$ | 40.5% | 25.4% | — | — | 100% | 100% |
| | $ZrO_2$ | 39.5% | 37.8% | — | — | 100% | 100% |
| | $TiO_2$ | 33.5% | 32.5% | — | — | 100% | 100% |
| | $Al_2O_3$ | 71.8% | 89.6% | — | — | 100% | 100% |

Example 12

In this example, combinatorial batch processes were evaluated using 3 wt % Pd and 6 wt % Re on various types of support material. The reactions were run using reaction conditions of 150° C., 3447.4 kPa (500 psig) $H_2$, a reaction time of 0.5 hours, and a catalyst concentration of 2 wt % of the total feed. Results for the different carbon support materials under these conditions are presented in Table 7.

TABLE 7

| | Conversion | | Xylene Selectivity | | Methyl Benzyl Alcohol Selectivity | |
|---|---|---|---|---|---|---|
| | p | o | p | o | p | o |
| $Nb_2O_5$ | 93.4% | 96.3% | 80.4% | 86.5% | 19.6% | 13.5% |
| $ZrO_2$ | 100.0% | 100.0% | 15.3% | 19.3% | 84.7% | 80.7% |
| ZSM-5 | 73.5% | 75.9% | 4.9% | 2.3% | 95.1% | 97.7% |
| Silica | 82.8% | 85.2% | 0.8% | 2.4% | 99.2% | 97.6% |
| $Al_2O_3$ | 100.0% | 100.0% | 12.9% | 17.7% | 87.1% | 82.3% |
| $TiO_2$ | 100.0% | 100.0% | 16.6% | 17.9% | 83.4% | 82.1% |

Example 13

Figure 12:
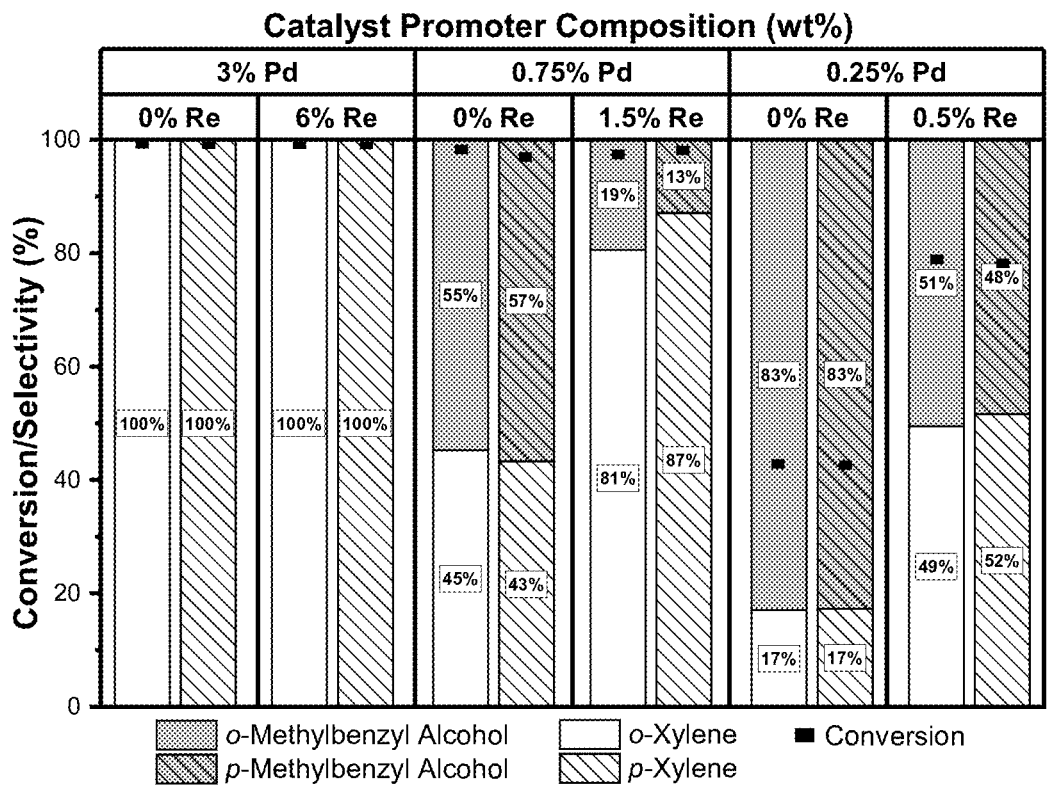
FIG. 12 shows conversion and selectivity (%) results obtained for a hydrogenation step using a batch combinatorial protocol, wherein a mixture comprising ortho/para methylbenzaldehyde was reacted with a Pd catalyst (with and without a Re modifier component) at different Pd loadings (i.e., 3 wt %, 0.75 wt %, and 0.25 wt %).

In this example, combinatorial batch processes were evaluated using 3 wt % Pd, 0.75 wt % Pd, and 0.25 wt % Pd with and without Re. The reactions were run using reaction conditions comprising 125° C., 1723.7 kPa (250 psig) $H_2$, and a reaction time of 30 minutes at 2.8 wt % catalyst loading on total feed. Results for this example are presented in FIG. 12.

Example 14

Figure 13:
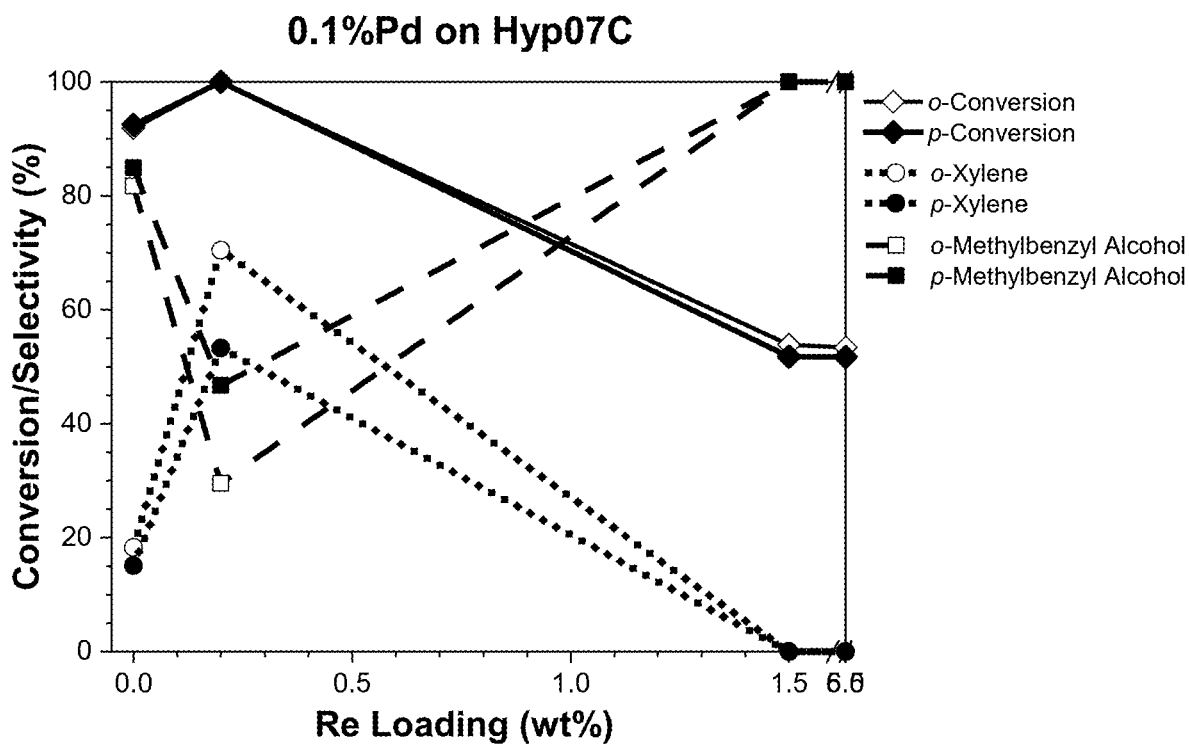
FIG. 13 shows conversion and selectivity (%) results obtained for a hydrogenation step using a batch combinatorial protocol, wherein a mixture comprising ortho/para methylbenzaldehyde was reacted with a Pd catalyst and a Re modifier component at different Pd:Re ratios wherein 0.1 wt % Pd was used with varying amounts of Re.

In this example, combinatorial batch processes were evaluated using 0.1 wt % Pd and varying amounts of Re (0.25 wt %, 1.5 wt %, and 6 wt %). The reactions were run using reaction conditions comprising 125° C., 1723.7 kPa (250 psig) $H_2$, and a reaction time of 30 minutes at 2.8 wt % catalyst loading on total feed. Results for this example are presented in FIG. 13.

Example 15

Figure 14:
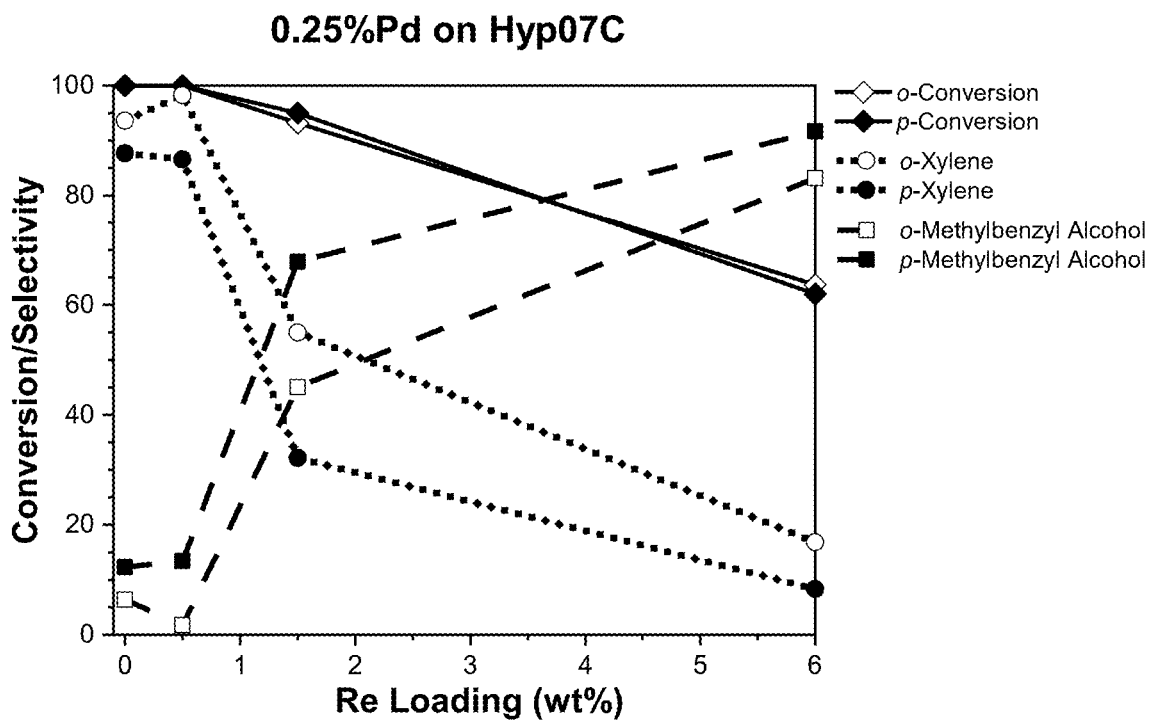
FIG. 14 shows conversion and selectivity (%) results obtained for a hydrogenation step using a batch combinatorial protocol, wherein a mixture comprising ortho/para methylbenzaldehyde was reacted with a Pd catalyst and a Re modifier component at different Pd:Re ratios wherein 0.25 wt % Pd was used with varying amounts of Re.

In this example, combinatorial batch processes were evaluated using 0.25 wt % Pd and varying amounts of Re (0.25 wt %, 1.5 wt %, and 6 wt %). The reactions were run using reaction conditions comprising 125° C., 1723.7 kPa (250 psig) $H_2$, and a reaction time of 30 minutes at 2.8 wt % catalyst loading on total feed. Results for this example are presented in FIG. 14.

Example 16

Figure 15:
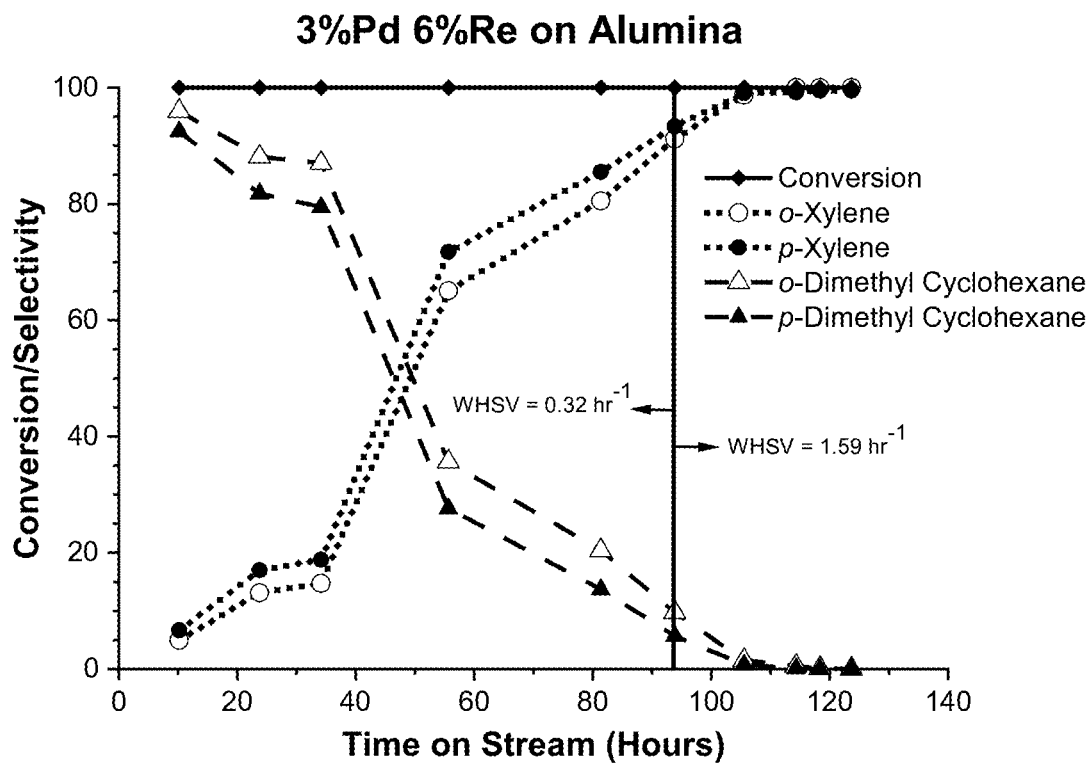
FIG. 15 shows conversion and selectivity (%) results obtained for a hydrogenation step using a flow reactor protocol, wherein a mixture comprising ortho/para methylbenzaldehyde was reacted with a Pd catalyst and a Re modifier component (3 wt % Pd and 6 wt % Re) on a carbon support.

In this example, a flow reactor was used to evaluate performance of a hydrogenation catalyst comprising Pd, Re, and an alumina support material (BASF-AL3945). The catalyst comprised 3 wt % Pd and 6 wt % Re. The reaction was run using reaction conditions comprising 180° C., 3102.6 kPa (450 psig) $H_2$, at 1.59 $hr^{-1}$ WHSV for a time on stream of over 120 hours. Results for this example are presented in FIG. 15.

Example 17

Figure 16:
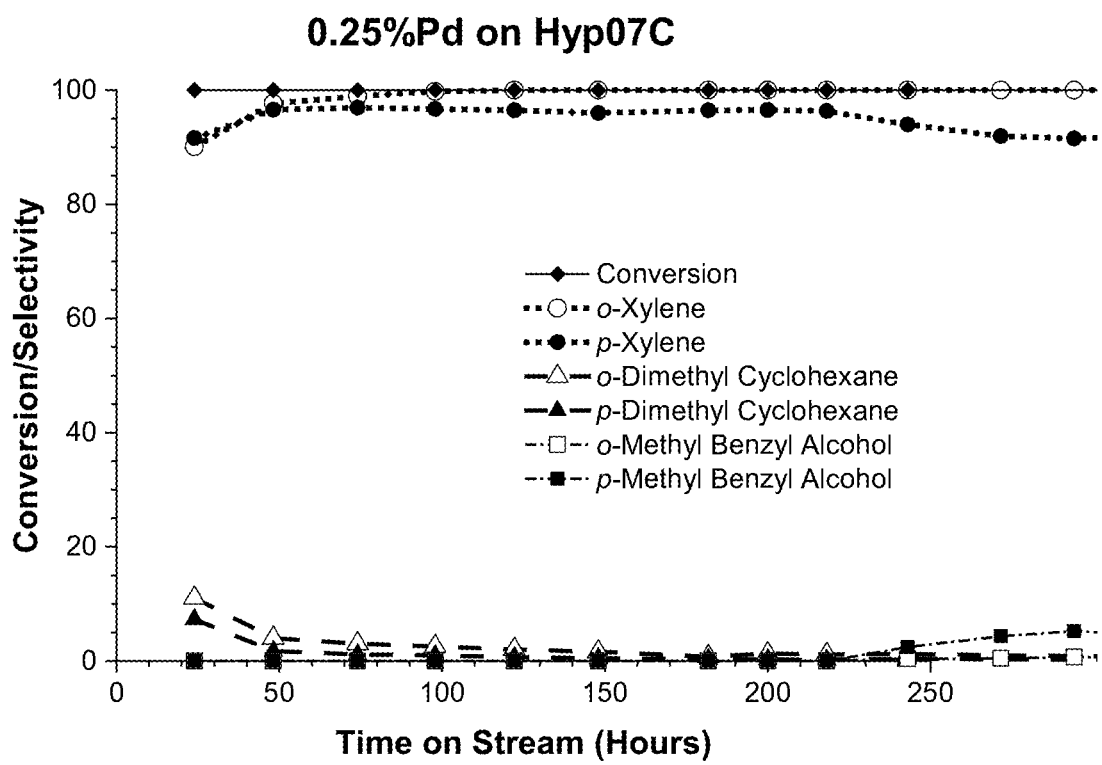
FIG. 16 shows conversion and selectivity (%) results obtained for a hydrogenation step using a flow reactor protocol, wherein a mixture comprising ortho/para methylbenzaldehyde was reacted with a Pd catalyst (0.25 wt %) without a Re modifier component on a carbon support.

In this example, a flow reactor was used to evaluate performance of a hydrogenation catalyst comprising 0.25 wt % Pd on carbon support material (namely, Hyp07C). The reaction was run using reaction conditions comprising 180° C., 3102.6 kPa (450 psig) $H_2$, at 1.32 $hr^{-1}$ WHSV for a time on stream of over 200 hours. Results for this example are presented in FIG. 16.

Example 18

Figure 17:
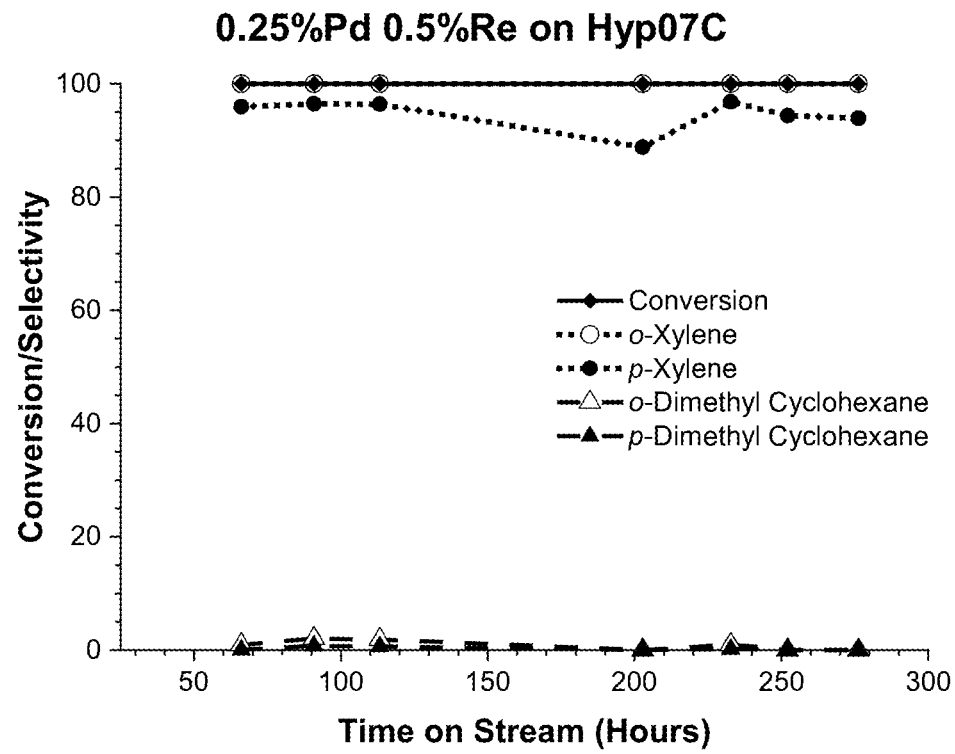
FIG. 17 shows conversion and selectivity (%) results obtained for a hydrogenation step using a flow reactor protocol, wherein a mixture comprising ortho/para methylbenzaldehyde was reacted with a Pd catalyst and a Re modifier component (0.25 wt % Pd and 0.5 wt % Re) on a carbon support.

In this example, a flow reactor was used to evaluate performance of a hydrogenation catalyst comprising Pd, Re, and a carbon support material (namely, Hyp07C). The catalyst comprised 0.25 w % Pd and 0.5 wt % Re. The reaction was run using reaction conditions comprising 180° C., 3102.6 kPa (450 psig) $H_2$, at 1.32 $hr^{-1}$ WHSV for a time on stream of over 250 hours. Results for this example are presented in FIG. 17.

Example 19

Figure 18:
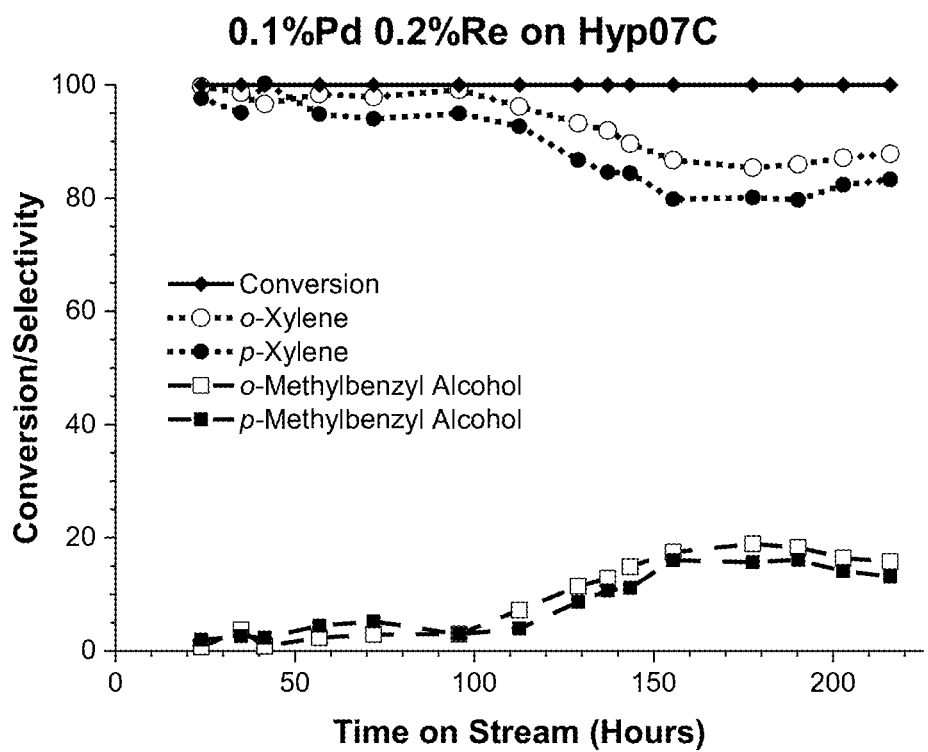
FIG. 18 shows conversion and selectivity (%) results obtained for a hydrogenation step using a flow reactor protocol, wherein a mixture comprising ortho/para methylbenzaldehyde as reacted with a Pd catalyst and a Re modifier component (0.1 wt % Pd and 0.2 wt % Re) on a carbon support.

In this example, a flow reactor was used to evaluate performance of a hydrogenation catalyst comprising Pd, Re, and a carbon support material (namely, Hyp07C). The catalyst comprised 0.1 w % Pd and 0.2 wt % Re. The reaction was run using reaction conditions comprising 180° C., 6894.8 kPa (1000 psig) $H_2$, at 2.32 $hr^{-1}$ WHSV for a time on stream of over 200 hours. Results for this example are presented in FIG. 18.

Example 20

Figure 19:
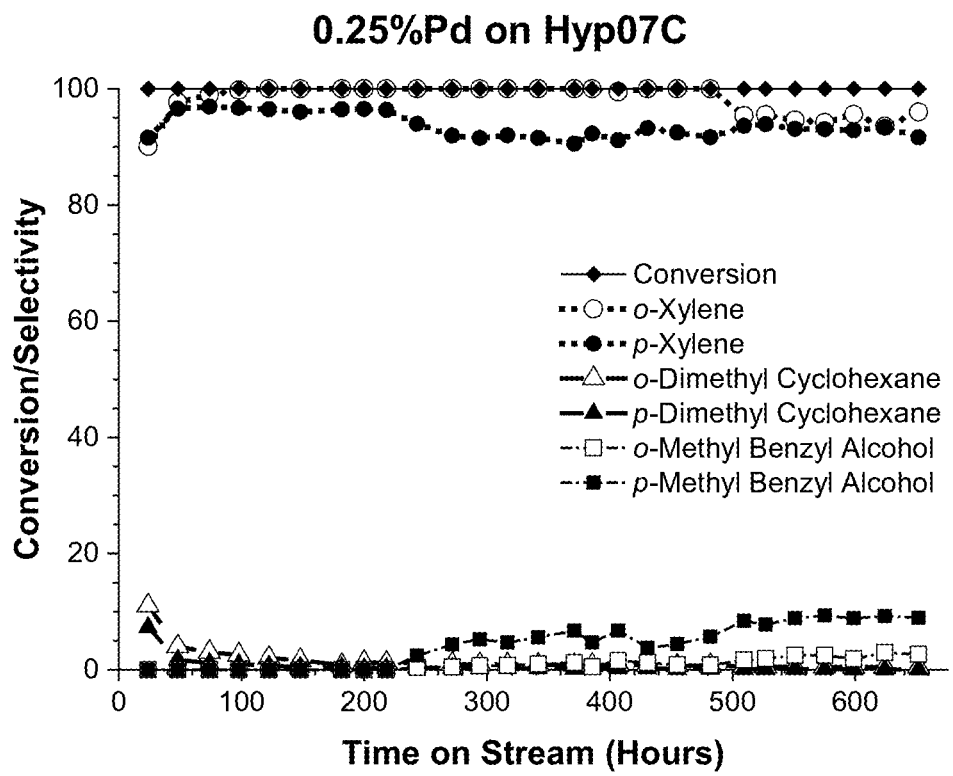
FIG. 19 shows conversion and selectivity (%) results obtained for a hydrogenation step using a flow reactor protocol, wherein a mixture comprising ortho/para methylbenzaldehyde was reacted with a Pd catalyst (0.25 wt %) without a Re modifier component on a carbon support for at least 600 hours, time on stream.

In this example, a flow reactor was used to evaluate performance of a hydrogenation catalyst comprising 0.25 wt % Pd on carbon support material (namely, Hyp07C. The reaction was run using reaction conditions comprising 180° C., 3102.6 kPa (450 psig) $H_2$, at 1.32 $hr^{-1}$ WHSV for a time on stream of over 600 hours. Results for this example are presented in FIG. 19.

Example 21

Figure 20:
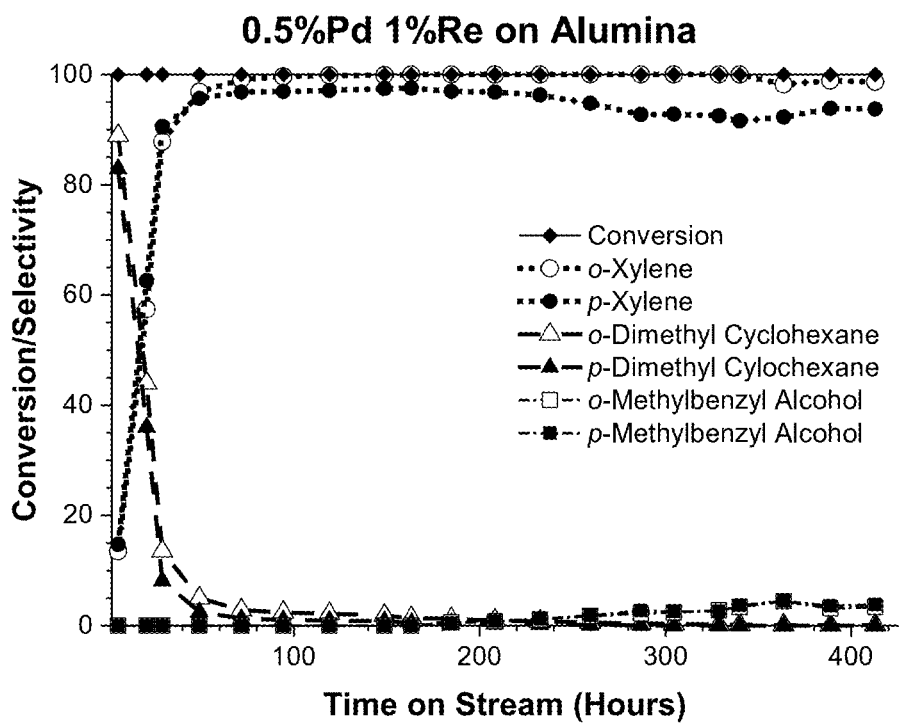
FIG. 20 shows conversion and selectivity (%) results obtained for a hydrogenation step using a flow reactor protocol, wherein a mixture comprising ortho/para methylbenzaldehyde was reacted with a Pd catalyst and a Re modifier component (0.5 wt % Pd and 1 wt % Re) on a carbon support for at least 400 hours, time on stream.

In this example, a flow reactor was used to evaluate performance of a hydrogenation catalyst comprising Pd, Re, and an alumina support material (BASF-AL3945). The catalyst comprised 0.5 wt % Pd and 1 wt % Re. The reaction was run using reaction conditions comprising 180° C., 3102.6 kPa (450 psig) $H_2$, at 1.32 $hr^{-1}$ WHSV for a time on stream of over 400 hours. Results for this example are presented in FIG. 20.

In view of the many possible embodiments to which the principles of the present disclosure may be applied, it should be recognized that the illustrated embodiments are only preferred examples and should not be taken as limiting the scope of the disclosure. Rather, the scope is defined by the following claims. We therefore claim as our invention all that comes within the scope and spirit of these claims.

We claim:

1. A method, comprising:
   contacting a feed stream comprising ethanol with an oxidation catalyst under oxidation conditions to form an oxidation zone effluent stream comprising acetaldehyde;
   passing the oxidation zone effluent stream to a dimerization zone and contacting the oxidation zone effluent stream with a dimerization catalyst under dimerization conditions to produce a dimerization zone effluent stream comprising 2-butenal;
   passing the dimerization zone effluent stream to a cyclization zone and contacting the dimerization zone effluent stream with a cyclization catalyst under cyclization conditions to form a cyclization zone effluent stream comprising o-methylbenzaldehyde and/or p-methylbenzaldehyde; and
   passing the cyclization zone effluent stream to a hydrogenation zone and contacting the cyclization zone effluent stream with a hydrogenation catalyst comprising a first Group VIII metal deposited on a support material to produce a hydrogenation zone effluent comprising a non-equilibrium mixture of xylenes.

2. The method of claim 1, wherein the hydrogenation catalyst further comprises a second Group VIII metal, a modifier component, or a combination thereof, all deposited on the support material wherein the second Group VIII metal is not the same as the first Group VIII metal.

3. The method of claim 2, wherein the modifier component is selected from rhenium, tin, an alkali metal, an alkali earth metal, or any combination thereof.

4. The method of claim 2, wherein the hydrogenation catalyst comprises the modifier component and wherein the support material is carbon, the first Group VIII metal is palladium, and the modifier component is rhenium.

5. The method of claim 1, wherein the support material is selected from carbon material, a silica, an alumina, a silica-alumina, a titania, a zirconia, a zeolite, a zinc oxide, or any combination thereof.

6. The method of claim 1, wherein the non-equilibrium mixture of xylenes comprises m-xylene in an amount ranging from 0 wt % to less than 40 wt % of a m-xylene equilibrium concentration.

7. The method of claim 1, wherein the non-equilibrium mixture of xylenes comprises m-xylene in an amount ranging from 0 wt % to 20 wt % of a m-xylene equilibrium concentration.

8. The method of claim 1, wherein the non-equilibrium mixture of xylenes comprises m-xylene in an amount ranging from 0 wt % to 5 wt % of a m-xylene equilibrium concentration.

9. The method of claim 1, wherein the non-equilibrium mixture of xylenes comprises m-xylene in an amount ranging from 0 wt % to 1 wt % of a m-xylene equilibrium concentration.

10. The method of claim 1, wherein the ethanol is
  (i) ethanol from liquid phase fermentation of cellulosic material and or sugar;
  (ii) ethanol from gas phase fermentation of industrial process waste or non-waste gas, internal combustion engine exhaust fumes, syngas, direct air capture, electrolysis, $CO_2$-containing gas or any combination thereof;
  (iii) ethanol from a source other than cellulosic material, sugar, industrial process waste or non-waste gas, internal combustion engine exhaust fumes, gasification processes, syngas, direct air capture, electrolysis, or $CO_2$-containing gas; or
  (iv) ethanol from hydration of ethylene;
  or any combination of (i), (ii), (iii), and/or (iv).

11. The method of claim 10, wherein the industrial process is selected from ferrous metal products manufacturing, steel mill manufacturing, non-ferrous products manufacturing, petroleum refining, electric power production, carbon black production, paper and pulp production, ammonia production, methanol production, coke manufacturing, petrochemical production, carbohydrate fermentation, cellulosic fermentation, cement making, aerobic digestion, anerobic digestion, catalytic processes, natural gas extraction, oil extraction or any combination thereof; and/or wherein the syngas is from coal gasification, refinery residues gasification, petroleum coke gasification, biomass gasification, lignocellulosic material gasification, waste wood gasification, black liquor gasification, natural gas reforming, municipal solid or liquid waste gasification, refuse derived fuel gasification, sewerage or sewerage sludge gasification, sludge from waste water treatment gasification and/or industrial solid waste gasification or any combination thereof.

12. The method of claim 1, wherein:
  (i) the conversion of acetaldehyde in the dimerization zone provides 15 wt % to 65 wt % of a product reaction mixture comprising 2-butenal;
  (ii) the selectivity of acetaldehyde to 2-butenal in the dimerization zone ranges from 57 wt % to 91 wt %;
  (iii) the conversion of 2-butenal in the cyclization zone provides 70 wt % to 95 wt % of a product reaction mixture comprising o-methylbenzaldehyde and p-methylbenzaldehyde;
  (iv) the selectivity of 2-butenal to o-methylbenzaldehyde and p-methylbenzaldehyde in the cyclization zone ranges from 50 wt % to 95 wt %; or
  (v) any combination of (i), (ii), (iii), and/or (iv).

13. The method of claim 1, further comprising passing the hydrogenation zone effluent to a fractionation zone and separating a stream comprising o-xylene from (i) a stream comprising p-xylene or (ii) a stream comprising p-xylene and m-xylene.

14. The method of claim 13, wherein (i) the stream comprising p-xylene or (ii) the stream comprising p-xylene and m-xylene comprises a minimum amount of p-xylene, wherein the minimum amount of p-xylene ranges from a minimum of at least 65 wt % to a minimum of at least 85 wt %.

15. The method of claim 13, further comprising (i) drying the stream comprising the o-xylene; (ii) reacting the o-xylene in the stream comprising o-xylene under reaction conditions to form phthalic anhydride; or both (i) and (ii).

16. The method of claim 15, further comprising drying the hydrogenation zone effluent prior to passing it to the fractionation zone, and/or drying the stream comprising the o-xylene.

17. The method of claim 13, further comprising passing (i) the stream comprising p-xylene or (ii) the stream comprising p-xylene and m-xylene to a crystallizer and recovering a purified p-xylene stream comprising at least 99.5 wt % p-xylene.

18. The method of claim 17, wherein the purified p-xylene stream comprises at least 99.8 wt % p-xylene.

19. The method of claim 17, further comprising reacting at least a portion of the p-xylene from the purified p-xylene stream under reaction conditions to form terephthalic acid.

20. The method of claim 19, further comprising reacting at least a portion of the terephthalic acid with ethylene glycol under reaction conditions to form polyethylene terephthalate.

21. The method of claim 20, further comprising forming the polyethylene terephthalate into one or more products.

22. The method of claim 1, further comprising one or more separation and/or recycling steps, wherein the recycling steps are selected from
  (i) recycling at least a portion of the oxidation zone effluent stream to the oxidation zone until a predetermined target concentration of acetaldehyde in the oxidation zone effluent stream is achieved;
  (ii) recycling at least a portion of the dimerization zone effluent stream to the dimerization zone until a predetermined target concentration of 2-butenal in the dimerization zone effluent stream is achieved;
  (iii) recycling at least a portion of the cyclization zone effluent stream to the cyclization zone until a predetermined target concentration of o-methylbenzaldehyde and/or p-methylbenzaldehyde in the cyclization zone effluent stream is achieved;
  (iv) recycling at least a portion of the hydrogenation zone effluent stream to the hydrogenation zone until a predetermined target concentration of xylenes in the hydrogenation zone effluent stream is achieved; and/or
  (v) any combination of steps (i), (ii), (iii), and/or (iv).

23. The method of claim 1, further comprising regenerating the cyclization catalyst by heating the cyclization catalyst under air.

* * * * *